United States Patent [19]
Bemis et al.

[11] Patent Number: 6,025,147
[45] Date of Patent: *Feb. 15, 2000

[54] INHIBITORS OF INTERLEUKIN-1 β CONVERTING ENZYME

[75] Inventors: Guy W. Bemis, Arlington, Mass.; Julian M. C. Golec, Ashbury, United Kingdom; David J. Lauffer, Stow; Michael D. Mullican, Needham, both of Mass.; Mark A. Murcko, Holliston, Mass.

[73] Assignee: Vertex Pharmaceuticals, Inc., Cambridge, Mass.

[ * ] Notice: This patent issued on a continued prosecution application filed under 37 CFR 1.53(d), and is subject to the twenty year patent term provisions of 35 U.S.C. 154(a)(2).

[21] Appl. No.: 08/460,973

[22] Filed: Jun. 5, 1995

Related U.S. Application Data

[62] Division of application No. 08/261,452, Jun. 17, 1994, Pat. No. 5,756,466.

[51] Int. Cl.[7] .................................................. G01N 33/53

[52] U.S. Cl. .............................. 435/7.6; 435/7.4; 435/4

[58] Field of Search .............................. 435/4, 7.4, 7.6; 530/329–331

[56] References Cited

U.S. PATENT DOCUMENTS

| | | | |
|---|---|---|---|
| 4,276,298 | 6/1981 | Jones et al. | 424/270 |
| 4,369,183 | 1/1983 | Jones et al. | 424/263 |
| 4,499,295 | 2/1985 | Mueller et al. | 560/53 |
| 4,551,279 | 11/1985 | Mueller et al. | 260/404 |
| 4,584,397 | 4/1986 | Mueller et al. | 560/75 |
| 4,968,607 | 11/1990 | Dower et al. | 435/69.1 |
| 5,008,245 | 4/1991 | Digenis et al. | 514/18 |
| 5,055,451 | 10/1991 | Krantz et al. | 514/19 |
| 5,081,228 | 1/1992 | Dower et al. | 530/35.1 |
| 5,158,936 | 10/1992 | Krantz et al. | 514/19 |
| 5,180,812 | 1/1993 | Dower et al. | 530/351 |
| 5,374,623 | 12/1994 | Zimmerman et al. | 514/17 |
| 5,411,985 | 5/1995 | Bills et al. | 514/460 |
| 5,416,013 | 5/1995 | Black et al. | 435/226 |
| 5,430,128 | 7/1995 | Chapman et al. | 530/330 |
| 5,434,248 | 7/1995 | Chapman et al. | 530/330 |
| 5,462,939 | 10/1995 | Dolle et al. | 514/231.5 |
| 5,486,623 | 1/1996 | Zimmerman et al. | 549/417 |
| 5,498,616 | 3/1996 | Mallamo et al. | 514/300 |
| 5,498,695 | 3/1996 | Daumy et al. | 530/331 |
| 5,552,400 | 9/1996 | Dolle et al. | 514/221 |
| 5,565,430 | 10/1996 | Dolle et al. | 514/19 |
| 5,585,357 | 12/1996 | Dolle et al. | 514/18 |
| 5,585,486 | 12/1996 | Dolle et al. | 544/182 |
| 5,639,745 | 6/1997 | Dolle et al. | 514/183 |
| 5,670,494 | 9/1997 | Dolle et al. | 514/86 |

FOREIGN PATENT DOCUMENTS

| | | | |
|---|---|---|---|
| A-0 275 101 | 7/1988 | European Pat. Off. | C07K 5/02 |
| A-0 410 411 | 1/1991 | European Pat. Off. | C07K 5/04 |
| A-0 417 721 | 3/1991 | European Pat. Off. | C07K 5/10 |
| A-0 479 489 | 4/1992 | European Pat. Off. | C07K 5/08 |
| A-0 504 938 | 9/1992 | European Pat. Off. | A61K 37/02 |
| A-0 519 748 | 12/1992 | European Pat. Off. | C07K 5/04 |
| A-0 525 420 | 2/1993 | European Pat. Off. | C07D 307/56 |
| A-0 528 487 | 2/1993 | European Pat. Off. | C07K 5/10 |
| 0 533 350 A1 | 3/1993 | European Pat. Off. | C12N 15/57 |
| A-0 529 713 | 3/1993 | European Pat. Off. | B01J 20/32 |
| A-0 533 226 | 3/1993 | European Pat. Off. | C07K 5/10 |
| A-0 547 699 | 6/1993 | European Pat. Off. | C07K 5/02 |
| WO 91/15577 | 10/1991 | WIPO | C12N 9/64 |
| WO 93/05071 | 3/1993 | WIPO | C07K 13/00 |
| WO 93/09135 | 5/1993 | WIPO | C07K 5/04 |
| WO 93/14777 | 8/1993 | WIPO | A61K 37/00 |
| WO 93/16710 | 9/1993 | WIPO | A61K 37/00 |
| WO 93/25683 | 12/1993 | WIPO | C12N 15/12 |
| WO 93/25685 | 12/1993 | WIPO | C12N 15/12 |
| WO 93/25694 | 12/1993 | WIPO | C12N 15/57 |
| WO 94/00154 | 1/1994 | WIPO | A61K 39/395 |
| WO94/03480 | 2/1994 | WIPO | C07K 5/02 |

OTHER PUBLICATIONS

Fan, T.–P.D. et al., "Stimulation of Angiogenesis by Substance P and Interleukin–1 in the Rat and Its Inhibition by $NK_1$ or Interleukin–1 Receptor Antagonists" *Br. J. Pharmacol.*, 110, pp. 43–49 (1993).

Fauszt, I. et al., "Inhibition of Interleukin–1β Converting Enzyme by Peptide Derivatives" *Proc. of the 13th Am. Peptide Symp.*, Jun. 20–25, 1993, Hodges, R.S. and Smith, J.A., Eds., *Peptides*, pp. 589–591 (1994).

Hanessian, S. et al., "Design and Synthesis of a Prototype Model Antagonist of Tachykinin NK–2 Receptor" *Bioorg. Med. Chem. Lett.*, 11, pp. 1397–1400 (1994).

Mjalli, A.M.M. et al., "Phenylalkyl Ketones as Potent Reversible Inhibitors of Interkeukin–1β Converting Enzyme" *Bioorg. Med. Chem. Lett.*, 3, pp. 2689–2692 (1993).

Mullican, M.D. et al., "The Synthesis and Evaluation of Peptidyl Aspartyl Aldehydes as Inhibitors of ICE" *Bioorg. Med. Chem. Lett.*, 4, pp. 2359–2364 (1994).

(List continued on next page.)

*Primary Examiner*—Ponnathapura Achutamurthy
*Assistant Examiner*—T. Wessendorf
*Attorney, Agent, or Firm*—Fish & Neave; James F. Haley, Jr.; Lisa A. Dixon

[57] ABSTRACT

The present invention relates to novel classes of compounds which are inhibitors of interleukin-1β converting enzyme. The ICE inhibitors of this invention are characterized by specific structural and physicochemical features. This invention also relates to pharmaceutical compositions containing these compounds. The compounds and pharmaceutical compositions of this invention are particularly well suited for inhibiting ICE activity and consequently, may be advantageously used as agents against interleukin-1 mediated diseases, including inflammatory diseases, autoimmune diseases and neurodegenerative diseases. This invention also relates to methods for inhibiting ICE activity and methods for treating interleukin-1 mediated diseases using the compounds and compositions of this invention.

2 Claims, No Drawings

OTHER PUBLICATIONS

Robinson, R.P. and Donahue, K.M., "Synthesis of a Peptidyl Difluoro Ketone Bearing the Aspartic Acid Side Chain: An Inhibitor of Interleukin–1β Converting Enzyme" *J. Org. Chem.,* 57, pp. 7309–7314 (1992).

Salvatore, M.J. et al., "L–741,494, A Fungal Metabolite that is an Inhibitor of Interleukin–1β Converting Enzyme" *J. Nat. Prods.,* 57, pp. 755–760 (1994).

Spatola, A.F., in "Chemistry and Biochemistry of Amino Acids, Peptides, and Proteins," ch. 5, pp. 267–281, Weinstein, B., ed., Marcel Dekker, Inc., New York (1983).

N.P.C. Walker, et al., in "Crystal Structure of the Cysteine Protease Interleukin–1β–Converting Enzyme: A $(p20/p10)_2$ Homodimer", *Cell,* vol. 78, pp. 343–352 (Jul. 29, 1994).

Keith P. Wilson, et al., in "Structure and mechanism of interleukin–1β converting enzyme", *Nature,* vol. 370, pp. 270–275 (Jul. 28, 1994).

D. Alberg & S. Schreiber, "Structure–Based Design of a Cyclophilin–Calcineurin Bridging Ligand", *Science,* 262, pp. 248–250 (1993).

P. Andrews, "Functional Groups, Drug–Receptor Interactions and Drug Design", *Trends Pharmacol. Sci.,* 7, pp. 148–151 (1986).

K. Appelt et al., "Design of Enzyme Inhibitors Using Iterative Protein Crystallographic Analysis", *J. Med. Chem.,* 34, pp. 1925–1934 (1991).

E. Baker & J. Drenth, "The Thiol Proteases: Structure and Mechanism", in *Biological Macromolecules and Assemblies,* 3, pp. 313–368 (F. Jurnak & A. McPherson eds., 1987).

J. Baldwin et al., "Thienothiopyran–2–sulfonamides: Novel Topically Active Carbonic Anhydrase Inhibitors for the Treatment of Glaucoma", *J. Med. Chem.,* 32, pp. 2510–2513 (1989).

M. Barinaga, "Death Gives Birth to the Nervous System. But How?", *Science,* 259, pp. 762–763 (1993).

P. Bartlett et al., "Caveat: A Program to Facilitate the Structure–derived Design of Biologically Active Molecules", *Molecular Recognition: Chemical and Biochemical Problems,* 78, pp. 182–196 (1989).

P. Bender & J. Lee, "Pharmacological Modulation of Interleukin–1", *Annu. Rep. Med. Chem.,* 25, pp. 185–193 (1989).

R. Black et al., "Activation of Interleukin–1β by a Co–induced Protease", *FEBS Lett,* 247, pp. 386–390 (1989).

H. Böhm, "The Computer Program LUDI: A New Method for the De Novo Design of Enzyme Inhibitors", *J. Comput. Aided Mol. Des.,* 6, pp. 61–78 (1992).

J. Breitner et al., "Inverse Association of Anti–inflammatory Treatments and Alzheimer's Disease: Initial Results of a Co–twin Control Study", *Neurology,* 44, pp. 227–232 (1994).

B. Brooks et al., "CHARMM: A Program for Macromolecular Energy, Minimization, and Dynamics Calculations", *J. Comput. Chem.,* 4, pp. 187–217 (1983).

A. Brünger, "Extension of Molecular Replacement: A New Search Strategy Based on Patterson Correlation Refinement", *Acta Crystallogr. A,* 46, pp. 46–57 (1990).

A. Brünger & A. Krukowski, "Slow–Cooling Protocols for Crystallographic Refinement by Simulated Annealing", *Acta Crystallogr. A,* 46, pp. 585–593 (1990).

U. Burkett & N. Allinger, "Methods for the Computation of Molecular Geometry" in *Molecular Mechanics,* pp. 59–78 (1982).

M. Carson, "Ribbons 2.0", *J. App. Crystallogr.,* 24, pp. 958–961 (1991).

F. Casano et al., "The Structure and Complete Nucleotide Sequence of the Murine Gene Encoding Interleukin–1β Converting Enzyme (ICE)", *Genomics,* 20, pp. 474–481 (1994).

D. Cerretti et al., "Molecular Cloning of the Interleukin–1β Converting Enzyme", *Science,* 256, pp. 97–100 (1992).

K. Chapman, "Synthesis of a Potent, Reversible Inhibitor of Interleukin–1β Converting Enzyme", *Bioorg. Med. Chem. Lett.,* 2, pp. 613–618 (1992).

N. Cohen, "Drug Design in Three Dimensions", *Advances in Drug Research,* 14, pp. 41–145 (1985).

N. Cohen, "Rational Drug Design and Molecular Modeling", *Drugs of the Future,* 10, pp. 311–328 (1985).

N. Cohen et al., "Molecular Modeling Software and Methods for Medicinal Chemistry", *J. Med. Chem.,* 33, pp. 883–894 (1990).

D. Davies & D. Segal, "Protein Crystallization: Micro Techniques Involving Vapor Diffusion", *Methods Enzymol.,* 22, pp. 266–269 (1971).

K. Dill, "Dominant Forces in Protein Folding", *Biochemistry,* 29, pp. 7133–7155 (1990).

C. Dinarello, "Role of Interleukin–1 in Infectious Diseases", *Immunol. Rev.,* 127, pp. 119–146 (1992).

C. Dinarello et al., "Anticytokine Strategies in the Treatment of the Systemic Inflammatory Response Syndrome", *J. Am. Med. Assoc.,* 269, pp. 1829–1835 (1993).

R. Dolle et al., "$P_1$ Aspartate–Based Peptide α–((2, 6–Dichlorobenzoyl)oxy)methyl Ketones as Potent Time–Dependent Inhibitors of Interleukin–1β–Converting Enzyme", *J. Med. Chem.,* 37, pp. 563–564 (1994).

S. Ealick et al., "Application of Crystallographic and Modeling Methods in the Design of Purine Nucleoside Phosphorylase Inhibitors", *Proc. Natl. Acad. Sci. USA,* 88, pp. 11540–11544 (1991).

P. Edwards et al., "Design, Synthesis, and Kinetic Evaluation of a Unique Class of Elastase Inhibitors, the Peptidyl α–Ketobenzoxazoles, and the X–ray Crystal Structure of the Covalent Complex between Porcine Pancreatic Elastase and Ac–Ala–Pro–Val–2–Benzoxazole", *J. Am. Chem. Soc.,* 114, pp. 1854–1863 (1992).

H. Eklund et al., "Three–dimensional Structure of Horse Liver Alcohol Dehydrogenase at 2.4 Å Resolution", *J. Mol. Biol.,* 102, pp. 27–50 (1976).

J. Erickson et al., "Design, Activity, and 2.8 Å Crystal Structure of a $C_2$ Symmetric Inhibitor Complexed to HIV–1 Protease", *Science,* 249, pp. 527–533 (1990).

V. Gagliardini et al., "Prevention of Vertebrate Neuronal Death by the crmA Gene", *Science,* 263, pp. 826–828 (1994).

T. Geiger et al., "Neutralization of Interleukin–1β Activity in vivo with a Monoclonal Antibody Alleviates Collagen–induced Arthritis in DBA/1 Mice and Prevents the Associated Acute–phase Response", *Clin. Exp. Rheumatol.,* 11, pp. 515–522 (1993).

A. Giannis & T. Kolter, "Peptidomimetics for Receptor Ligands–Discovery, Development, and Medical Perspectives", *Angew. Chem. Int. Ed. Engl.* 32, pp. 1244–1267 (1993).

P. Goodford, "A Computational Procedure for Determining Energetically Favorable Binding Sites on Biologically Important Macromolecules", *J. Med. Chem.,* 28, pp. 849–857 (1985).

D. Goodsell & A. Olson, "Automated Docking of Substrates to Proteins by Simulated Annealing", *Proteins: Structure, Function, and Genetics*, 8, pp. 195–202 (1990).

T. Graybill et al., "The Preparation and Evaluation of Peptidic Aspartyl Hemiacetals as Reversible Inhibitors of ICE", *Am. Chem. Soc. Abs.* (*206th Natl. Mtg.*), 235 (1993).

W. Griffin et al., "Brain Interleukin 1 and S–100 Immunoreactivity are Elevated in Down Syndrome and Alzheimer Disease", *Proc. Natl. Acad. Sci. USA*, 86, pp. 7611–7615 (1989).

C. Hammerberg et al., "Interleukin–1 Receptor Antagonist in Normal and Psoriatic Epidermis", *J. Clin. Invest.*, 90, pp. 571–583 (1992).

E. Harris, "Rheumatoid Arthritis: Pathophysiology and Implications for Therapy", *N. Eng. J. Med.*, 322, pp. 1277–1289 (1990).

W. Hendrickson et al., "Selenomethionyl Proteins Produced for Analysis by Multiwavelength Anomalous Diffraction (MAD): A Vehicle for Direct Determination of Three–dimensional Structure", *EMBO J.*, 9, pp. 1665–1672 (1990).

R. Hirschmann et al., "The First Design and Synthesis of a Steroidal Peptidomimetic. The Potential Value of Peptidomimetics in Elucidating the Bioactive Conformation of Peptide Ligands", *J. Am. Chem. Soc.*, 114, pp. 9699–9701 (1992).

R. Hirschmann et al., "Nonpeptidal Peptidomimetics with a β–D–Glucose Scaffolding. A Partial Somatostatin Agonist Bearing a Close Structural Relationship to a Potent, Selective Substance P Antagonist", *J. Am. Chem. Soc.*, 114, pp. 9217–9218 (1992).

A. Holmgren et al., "Three–dimensional Structure of *Escherichia coli* Thioredoxin–$S_2$ to 2.8Å Resolution", *Proc. Natl. Acad. Sci. USA*, 72, pp. 2305–2309 (1975).

A. Hopfinger, "Computer–Assisted Drug Design", *J. Med. Chem.*, 28, pp. 1133–1139 (1985).

A. Hopfinger & B. Burke, "Molecular Shape Analysis: A Formalism to Quantitatively Establish Spatial Molecular Similarity", in *Concepts and Applications of Molecular Similarity*, pp. 173–209 (M. Johnson & G. Maggiora eds., 1990).

A. Howard et al., "High–Level Production and Characterization of Functional Human Interleukin–1β Converting Enzyme in Baculovirus and *E.coli* Expression Systems", *J. Cell. Biochem. Suppl.*, 17B, p. 146 (1993).

A. Howard et al., "Human Interleukin–1β Converting Enzyme: A Mutational Analysis of Proenzyme Activation", *J. Cell. Biochem. Suppl.*, 17B, p. 113 (1993).

A. Howard et al., "IL–1–Converting Enzyme Requires Aspartic Acid Residues for Processing of the IL–1β Precursor at Two Distinct Sites and Does Not Cleave 31–kDa IL–1α", *J. Immunol.*, 147, pp. 2964–2969 (1991).

I. Kamphuis et al., "Thiol Proteases: Comparative Studies Based on the High–resolution Structures of Papain and Actinidin, and on Amino Acid Sequence Information for Cathepins B and H, and Stem Bromelain", *J. Mol. Biol.*, 182, pp. 317–329 (1985).

J. Knowles, "Tinkering with Enzymes: What are We Learning?", *Science*, 236, pp. 1252–1258 (1987).

M. Kostura et al., "Identification of a Monocyte Specific Pre–Interleukin 1β Convertase Activity", *Proc. Natl. Acad. Sci. USA*, 86, pp. 5227–5231 (1989).

I. Kuntz et al., "A Geometric Approach to Macromolecule–Ligand Interactions", *J. Mol. Biol.*, 161, pp. 269–288 (1982).

E. Lattman, "Use of the Rotation and Translation Functions", *Methods Enzymol.*, 115, pp. 55–77 (1985).

C. Lipinski, "Bioisosterism in Drug Design", *Annu. Rep. Med. Chem.*, 21, pp. 283–291 (1986).

G. Lonnemann et al., "Differences in the Synthesis and Kinetics of Release of Interleukin 1α, Interleukin 1β and Tumor Necrosis Factor from Human Mononuclear Cells", *Eur. J. Immunol.*, 19, pp. 1531–1536 (1989).

T. Mandrup–Poulsen et al., "Involvement of Interleukin 1 and Interleukin 1 Antagonist in Pancreatic β–Cell Destruction in Insulin–dependent Diabetes Mellitus", *Cytokine*, 5, pp. 185–191 (1993).

C. March et al., "Cloning, Sequence and Expression of Two Distinct Human Interleukin–1 Complementary DNAs", *Nature*, 315, pp. 641–647 (1985).

G. Marshall, "Computer–Aided Drug Design", *Annu. Rev. Pharmacol. Toxicol.*, 27, pp. 193–213 (1987).

G. Marshall & I. Motoc, "Approaches to the Conformation of the Drug Bound to the Receptor", in *Molecular Graphics and Drug Design*, pp. 115–156 (A. Burgen et al. eds., 1986).

Y. Martin, "3D Database Searching in Drug Design", *J. Med. Chem.*, 35, pp. 2145–2154 (1992).

J. Marx, "Cell Death Studies Yield Cancer Clues", *Science*, 259, pp. 760–761 (1993).

D. Mayer et al., "A Unique Geometry of the Active Site of Angiotensin–Converting Enzyme Consistent with Structure–Activity Studies", *J. Comput. Aided Mol. Des.*, 1, pp. 3–16 (1987).

R. Ménard et al., "Contribution of the Glutamine 19 Side Chain to Transition–State Stabilization in the Oxyanion Hole of Papain", *Biochemistry*, 30, pp. 8924–8928 (1991).

R. Ménard et al., "Importance of Hydrogen–Bonding Interactions Involving the Side Chain of Asp 158 in the Catalytic Mechanism of Papain", *Biochemistry*, 30, pp. 5531–5538 (1991).

E. Meng et al., "Automated Docking with Grid–Based Energy Evaluation", *J. Comput. Chem.*, 13, pp. 505–524 (1992).

D. Miller et al., "The IL–1β Converting Enzyme as a Therapeutic Target", *Ann. N. Y. Acad. Sci.*, 696, pp. 133–148 (1993).

S. Miller et al., "The Accessible Surface Area and Stability of Oligomeric Proteins", *Nature*, 328, pp. 834–836 (1987).

A. Miranker & M. Karplus, "Functionality Maps of Binding Sites: A Multiple Copy Simultaneous Search Method", *Proteins: Structure, Function, and Genetics*, 11, pp. 29–34 (1991).

M. Miura et al., "Induction of Apoptosis in Fibroblasts by IL–1β–Converting Enzyme, a Mammalian Homolog of the *C.elegans* Cell Death Gene ced–3", *Cell*, 75, pp. 653–660 (1993).

S. Molineaux et al., "Interleukin 1β (IL–1β) Processing in Murine Macrophages Requires a Structurally Conserved Homologue of Human IL–1β Converting Enzyme", *Proc. Natl. Acad. Sci. USA*, 90, pp. 1809–1813 (1993).

B. Mosley et al., "Determination of the Minimum Polypeptide Lengths of the Functionally Active Sites of Human Interleukins 1α and 1β", *Proc. Natl. Acad. Sci. USA*, 84, pp. 4572–4576 (1987).

M. Navia & M. Murcko, "Use of Structural Information in Drug Design", *Curr. Opin. Struc. Biol.*, 2, pp. 202–210 (1992).

M. Nett et al., "Molecular Cloning of the Murine IL–1β Converting Enzyme cDNA", *J. Immunol.*, 149, pp. 3254–3259 (1992).

M. Nett–Fiordalisi et al., "Characterization and Activation of the Murine Interleukin–1β (IL–1β) Converting Enzyme", *J.Cell. Biochem. Suppl.,* 17B, p. 117 (1993).

Y. Nishibata & A. Itai, "Automatic Creation of Drug Candidate Structures Based on Receptor Structure. Starting Point for Artificial Lead Generation", *Tetrahedron,* 47, pp. 8985–8990 (1991).

C. Noren et al., "A General Method for Site–Specific Incorporation of Unnatural Amino Acids into Proteins", *Science,* 244, pp. 182–188 (1989).

I. Noronha et al., "In situ Production of TNF–α, IL–1β and IL–2R in ANCA–positive Glomerulonephritis", *Kidney Int.,* 43,pp. 682–692 (1993).

K. Ohlsson et al., "Interleukin–1 Receptor Antagonist Reduces Mortality from Endotoxin Shock", *Nature,* 348, pp. 550–552 (1990).

J. Oppenheim et al., "There is More than One Interleukin 1", *Immunol. Today,* 7, pp. 45–55 (1986).

M. Pennington & N. Thornberry, "Synthesis of a Fluorogenic Interleukin–1β Converting Enzyme Substrate Based on Resonance Energy Transfer", *Pept. Res.,* 7, pp. 72–76 (1994).

R. Peters & R. McKinstry, "Three–Dimensional Modeling and Drug Development: Has "Rational" Drug Design Arrived?" *Biotechnology* (*N Y*), 12 pp. 147–150 (1994).

J. Plattner & D. Norbeck, "Obstacles to Drug Development from Peptide Leads", in *Drug Discovery Technologies,* pp. 92–126 (C. Clark & W. Moos eds., 1990).

L. Polgár, "On the Mode of Activation of the Catalytically Essential Sulfhydryl Group of Papain", *Eur. J. Biochem.,* 33, pp. 104–109 (1973).

C. Ray et al., "Viral Inhibition of Inflammation: Cowpox Virus Encodes an Inhibitor of the Interleukin–1β Converting Enzyme", *Cell,* 69, pp. 597–604 (1992).

L. Reiter, "Peptidic p–Nitroanilide Substrates of Interleukin–1β–Converting Enzyme", *Int. J. Pept. Protein Res.,* 43, pp. 87–96 (1994).

C. Ring et al., "Structure–based Inhibitor Design by Using Protein Models for the Development of Antiparasitic Agents", *Proc. Natl. Acad. Sci. USA,* 90, pp. 3583–3587 (1993).

J. Sandberg et al., "Treatment with an Interleukin–1 Receptor Antagonist Protein Prolongs Mouse Islet Allograft Survival", *Diabetes,* 42, pp. 1845–1851 (1993).

I. Schecter & A. Berger, "On the Size of the Active Site in Proteases. I. Papain", *Biochem. Biophys. Res. Commun.,* 27, pp. 157–162 (1967).

B. Shivers et al., "Molecular Cloning of Rat Interleukin–1β–Converting Enzyme: Distribution and Regulation", *J. Cell. Biochem. Suppl.,* 17B, p. 119 (1993).

I. Singer et al., "Interleukin 1β is Localized in the Cytoplasmic Ground Substance but is Largely Absent from the Golgi Apparatus and Plasma Membranes of Stimulated Human Monocytes", *J. Exp. Med.,* 167, pp. 389–407 (1988).

P. Sleath et al., "Substrate Specificity of the Protease that Processes Human Interleukin–1β", *J. Biol. Chem.,* 265, pp. 14526–14528 (1990).

R. Taylor & O. Kennard, "Hydrogen–Bond Geometry in Organic Crystals", *Acc. Chem. Res.,* 17, pp. 320–326 (1984).

C. Thornber, "Isosterism and Molecular Modification in Drug Design", *Chem. Soc. Rev.,* 8, pp. 563–580 (1979).

N. Thornberry et al., "A Novel Heterodimeric Cysteine Protease is Required for Interleukin–1β Processing in Monocytes", *Nature,* 356, pp. 768–774 (1992).

N. Thornberry et al., "Inactivation of Interleukin–1β Converting Enzyme by Peptide (Acyloxy)methyl Ketones", *Biochemistry,* 33, pp. 3934–3940 (1994).

J. Travis, "Proteins and Organic Solvents Make an Eye–Opening Mix", *Science,* 262, p. 1374 (1993).

P. Warner, et al., "Pyridone HLE Inhibitors: Variation of the 3 and 5 Substituents", *Royal Soc. Chem. Abs.* (*7th RSC–SCI Med. Chem. Symp.*), P23 (1993).

S. Weiner et al., "A New Force Field for Molecular Mechanical Simulation of Nucleic Acids and Proteins", *J. Am. Chem. Soc.,* 106, pp. 765–784 (1984).

C. Wong & J. McCammon, "Dynamics and Design of Enzymes and Inhibitors", *J. Am. Chem. Soc.,* 108, pp. 3830–3832 (1986).

P. Wooley et al., "The Effect of an Interleukin–1 Receptor Antagonist Protein on Type II Collagen–induced Arthritis and Antigen–induced Arthritis in Mice", *Arthritis Rheum.,* 36, pp. 1305–1314 (1993).

J. Yuan et al., "The *C.elegans* Cell Death Gene ced–3 Encodes a Protein Similar to Mammalian Interleukin–1β–Converting Enzyme", *Cell,* 75, pp. 641–652 (1993).

INHIBITORS OF INTERLEUKIN-1 β CONVERTING ENZYME

This is a division of application Ser. No. 08/261,452, filed Jun. 17, 1994, now U.S. Pat. No. 5,756,466 (May 26, 1998) entitled Inhibitors of Interleukin-1β Converting Enzyme.

TECHNICAL FIELD OF THE INVENTION

The present invention relates to novel classes of compounds which are inhibitors of interleukin-1β converting enzyme ("ICE"). The ICE inhibitors of this invention are characterized by specific structural and physicochemical features. This invention also relates to pharmaceutical compositions comprising these compounds. The compounds and pharmaceutical compositions of this invention are particularly well suited for inhibiting ICE activity and consequently, may be advantageously used as agents against interleukin-1 ("IL-1") mediated diseases, including inflammatory diseases, autoimmune diseases and neurodegenerative diseases. This invention also relates to methods for inhibiting ICE activity and methods for treating interleukin-1 mediated diseases using the compounds and compositions of this invention.

BACKGROUND OF THE INVENTION

Interleukin 1 ("IL-1") is a major pro-inflammatory and immunoregulatory protein that stimulates fibroblast differentiation and proliferation, the production of prostaglandins, collagenase and phospholipase by synovial cells and chondrocytes, basophil and eosinophil degranulation and neutrophil activation. Oppenheim, J. H. et al, *Immunology Today*, 7, pp. 45–56 (1986). As such, it is involved in the pathogenesis of chronic and acute inflammatory and autoimmune diseases. IL-1 is predominantly produced by peripheral blood monocytes as part of the inflammatory response and exists in two distinct agonist forms, IL-1α and IL-1β. Mosely, B. S. et al., *Proc. Nat. A-ad. Sci.*, 84, pp. 4572–4576 (1987); Lonnemann, G. et al., *Eur.J. Immunol.*, 19, pp. 1531–1536 (1989).

IL-1β is synthesized as a biologically inactive precursor, pIL-1β. pIL-1β lacks a conventional leader sequence and is not processed by a signal peptidase. March, C. J., *Nature*, 315, pp. 641–647 (1985). Instead, pIL-1β is cleaved by interleukin-1β converting enzyme ("ICE") between Asp-116 and Ala-117 to produce the biologically active C-terminal fragment found in human serum and synovial fluid. Sleath, P. R., et al., *J. Biol. Chem.*, 265, pp. 14526–14528 (1992); A. D. Howard et al., *J. Immunol.*, 147, pp. 2964–2969 (1991). Processing by ICE is also necessary for the transport of mature IL-1β through the cell membrane.

ICE is a cysteine protease localized primarily in monocytes. It converts precursor IL-1β to the mature form. Black, R. A. et al., *FEBS Lett.*, 247, pp. 386–390 (1989); Kostura, M. J. et al., *Proc. Natl. Acad. Sci. USA*, 86, pp. 5227–5231 (1989). ICE, or its homologues, also appears to be involved in the regulation of cell death or apoptosis. Yuan, J. et al., *Cell*, 75, pp. 641–652 (1993); Miura, M. et al., *Cell*, 75, pp. 653–660 (1993); Nett-Fiordalisi, M. A. et al., *J. Cell Biochem.*, 17B, p. 117 (1993). In particular, ICE or ICE homologues are thought to be associated with the regulation of apoptosis in neurogenerative diseases, such as Alzheimer's and Parkinson's disease. Marx, J. and M. Baringa, *Science*, 259, pp. 760–762 (1993); Gagliardini, V. et al., *Science*, 263, pp. 826–828 (1994).

ICE has been previously described as a heterodimer composed of two subunits, p20 and p10 (20 kDa and 10 kDa molecular weight, respectively). These subunits are derived from a 45 kDa proenzyme (p45) by way of a p30 form, through an activation mechanism that is autocatalytic. Thornberry, N. A. et al., *Nature*, 356, pp. 768–774 (1992). The ICE proenzyme has been divided into several functional domains: a prodomain (p14), a p22/20 subunit, a polypeptide linker and a p10 subunit. Thornberry et al., supra; Casano et al., *Genomics*, 20, pp. 474–481 (1994).

Full length p45 has been characterized by its cDNA and amino acid sequences. PCT patent applications WO 91/15577 and WO 94/00154. The p20 and p10 cDNA and amino acid sequences are also known. Thornberry et al., supra. Murine and rat ICE have also been sequenced and cloned. They have high amino acid and nucleic acid sequence homology to human ICE. Miller, D. K. et al.,*Ann. N.Y. Acad. Sci.*, 696, pp. 133–148 (1993); Molineaux, S. M. et al., *Proc. Nat. Acad. Sci.*, 90, pp. 1809–1813 (1993). Knowledge of the primary structure of ICE, however, does not allow prediction of its tertiary structure. Nor does it afford an understanding of the structural, conformational and chemical interactions of ICE and its substrate pIL-1β or other substrates or inhibitors.

ICE inhibitors represent a class of compounds useful for the control of inflammation or apoptosis or both. Peptide and peptidyl inhibitors of ICE have been described. PCT patent applications WO 91/15577; Wo 93/05071; WO 93/09135; WO 93/14777 and WO 93/16710; and European patent application 0 547 699. However, due to their peptidic nature, such inhibitors are typically characterized by undesirable pharmacologic properties, such as poor oral absorption, poor stability and rapid metabolism. Plattner, J. J. and D. W. Norbeck, in *Drug Discovery Technologies*, C. R. Clark and W. H. Moos, Eds. (Ellis Horwood, Chichester, England, 1990), pp. 92–126. This has hampered their development into effective drugs.

Accordingly, the need exists for compounds that can effectively inhibit the action of ICE, for use as agents for preventing and treating chronic and acute forms of IL-1 mediated diseases, including various cancers, as well as inflammatory, autoimmune or neurodegenerative diseases.

SUMMARY OF THE INVENTION

The present invention provides novel classes of compounds, and pharmaceutically acceptable derivatives thereof, that are useful as inhibitors of ICE. These compounds can be used alone or in combination with other therapeutic or prophylactic agents, such as antibiotics, immunomodulators or other anti-inflammatory agents, for the treatment or prophylaxis of diseases mediated by IL-1. According to a preferred embodiment, the compounds of this invention are capable of binding to the active site of ICE and inhibiting the activity of that enzyme.

It is a principal object of this invention to provide novel classes of inhibitors of ICE. These novel classes of ICE inhibitors are characterized by the following structural and physicochemical features:

a) a first and a second hydrogen bonding moiety, each of said moieties being capable of forming a hydrogen bond with a different backbone atom of ICE, said backbone atom being selected from the group consisting of the carbonyl oxygen of Arg-341, the amide —NH— group of Arg-341, the carbonyl oxygen of Ser-339 and the amide —NH— group of Ser-339;

b) a first and a second moderately hydrophobic moiety, said moieties each being capable of associating with a separate binding pocket of ICE when the inhibitor is bound thereto, said binding pocket being selected from the group consisting of the P2 binding pocket, the P3 binding pocket, the P4 binding pocket and the P' binding pocket; and c) an electronegative moiety comprising one or more electronegative atoms, said atoms being attached to the same atom or to adjacent atoms in the moiety and said moiety being capable of forming one or more hydrogen bonds or salt bridges with residues in the P1 binding pocket of ICE.

It is also an object of this invention to provide a method for identification, design or prediction of ICE inhibitors comprising the steps of:

a) selecting a candidate compound of defined chemical structure comprising at least two hydrogen bonding moieties, at least two moderately hydrophobic moieties and one electronegative moiety comprising one or more electronegative atoms attached either to the same atom or to adjacent atoms in the electronegative moiety;

b) determining a low-energy conformation for binding of said compound to the active site of ICE;

c) evaluating the capability of said compound in said conformation to form at least two hydrogen bonds with the non-carbon backbone atoms of Arg-341 and Ser-339 of ICE;

d) evaluating the capability of said compound in said conformation to associate with at least two of the binding pockets of ICE selected from the group consisting of the P2 binding pocket, the P3 binding pocket, the P4 binding pocket and the P' binding pocket;

e) evaluating the capability of said compound in said conformation to interact with the P1 binding pocket of ICE; and f) accepting or rejecting said candidate compound as an ICE inhibitor based on the determinations and evaluations carried out in the preceding steps.

It is a further object of this invention to provide novel classes of ICE inhibitors represented by formulas:

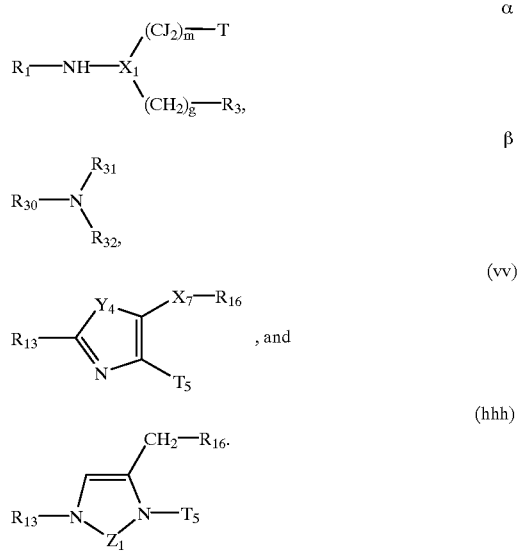

| ABBREVIATIONS AND DEFINITIONS | |
|---|---|
| Designation | Abbreviations Reagent or Fragment |
| Ala | alanine |
| Arg | arginine |
| Asn | asparagine |
| Asp | aspartic acid |
| Cys | cysteine |
| Gln | glutamine |
| Glu | glutamic acid |
| Gly | glycine |
| His | histidine |
| Ile | isoleucine |
| Leu | leucine |
| Lys | lysine |
| Met | methionine |
| Phe | phenylalanine |
| Pro | proline |
| Ser | serine |
| Thr | threonine |
| Trp | tryptophan |
| Tyr | tyrosine |
| Val | valine. |

Definitions

The following terms are employed herein:

The term "active site" refers to any or all of the following sites in ICE: the substrate binding site, the site where an inhibitor binds and the site where the cleavage of substrate occurs. The active site is characterized by at least amino acid residues: 173, 176, 177, 178, 179, 180, 236, 237, 238, 239, 244, 248, 283, 284, 285, 290, 338, 339, 340, 341, 342, 343, 344, 345, 348, 352, 381, 383, using the sequence and numbering according to Thornberry et al., supra.

The terms "P binding pocket", "S subsite", "S pocket", and the like, refer to binding subsites, or portions of the substrate binding site on the ICE molecule. The amino acid residues of the substrate are given designations according to their position relative to the scissile bond, i.e. the bond which is broken by the protease. The residues are designated P1, P2, etc., for those extending toward the N-terminus of the substrate and P1', P2', etc., for those extending toward the C-terminus of the substrate. The portions of an inhibitor which correspond to the P or P' residues of the substrate are also labeled P1, P1', etc., by analogy with the substrate. The binding subsites of the ICE molecule which receive the residues labeled P1, P1', etc., are designated S1, S1', etc., or may alternately be designated "the P1 binding pocket", "the P1' binding pocket", etc. [I. Schechter and A. Berger, "On the Size of the Active Site in Proteases", *Biochem. Biophys. Res. Commun.*, vol. 27, pp. 157–162 (1967).]

The terms "P2 binding pocket" or "S2 subsite" of the ICE active site are equivalent and are defined as the space surrounded by amino acid residues Pro-290, Val-338 or Trp-340.

The terms "P3 binding pocket" or "S3 subsite" of the ICE active site are equivalent and are defined as the space surrounded by amino acid residues Pro-177, Arg-178, Thr-180, Arg-341 or Pro-343.

The terms "P4 binding pocket" or "S4 subsite" of the ICE active site are equivalent and are defined as the space surrounded by amino acid residues His-342, Met-345, Val-348, Arg-352, Asp-381, Arg-383 or Trp-340.

The terms "P1 binding pocket" or "SI subsite" of the ICE active site are equivalent and are defined as the space surrounded by amino acid residues Arg-1,9, His-237, Gln-283, or Arg-341.

The terms "P' binding pocket" or "S' subsite" of the ICE active site are equivalent and are defined as the space surrounded by amino acid residues Phe-173, Ile-176, His-237, Gly-238, Ile-239, Cys-244 or His-248.

The term "hydrophobic" refers to a moiety which tends not to dissolve in water and is fat-soluble. Hydrophobic moieties include, but are not limited to, hydrocarbons, such as alkanes, alkenes, alkynes, cycloalkanes, cycloalkenes, cycloalkynes and aromatic compounds, such as aryls, certain saturated and unsaturated heterocycles and moieties that are substantially similar to the side chains of hydrophobic natural and unnatural α-amino acids, including valine, leucine, isoleucine, methionine, phenylanine, α-amino isobutyric acid, alloisoleucine, tyrosine, and tryptophan.

The term "moderately hydrophobic" refers to a hydrophobic moiety in which one or two carbon atoms have been replaced with more polar atoms, such as oxygen or nitrogen.

The term "heterocycle" or "heterocyclic" refers to a stable mono- or polycyclic compound which may optionally contain one or two double bonds or may optionally contain one or more aromatic rings. Each heterocycle consists of carbon atoms and from one to four heteroatoms independently selected from a group including nitrogen, oxygen, and sulfur. As used herein, the terms "nitrogen heteroatoms" and "sulphur heteroatoms" include any oxidized form of nitrogen or sulfur and the quaternized form of any basic nitrogen. Heterocycles defined above include, for example, pyrimidinyl, tetrahydroquinolyl, tetrahydroisoquinonlinyl, purinyl, pyrimidyl, indolinyl, benzimidazolyl, imidazolyl, imidazolinoyl, imidazolidinyl, quinolyl, isoquinolyl, indolyl, pyridyl, pyrrolyl, pyrrolinyl, pyrazolyl, pyrazinyl, quinoxolyl, piperidinyl, morpholinyl, thiamorpholinyl, furyl, thienyl, triazolyl, thiazolyl, β-carbolinyl, tetrazolyl, thiazolidinyl, benzofuranoyl, thiamorpholinyl sulfone, benzoxazolyl, oxopiperidinyl, oxopyrrolidinyl, oxoazepinyl, azepinyl, isoxazolyl, tetrahydropyranyl, tetrahydrofuranyl, thiadiazolyl, benzodioxolyl, benzothienyl, tetrahydrothiophenyl and sulfolanyl. Further heterocycles are described in A. R. Katritzky and C. W. Rees, eds., *Comprehensive Heterocyclic Chemistry: The Structure, Reactions, Synthesis and Use of Heterocyclic Compounds*, Vol. 1–8, Pergamon Press, NY (1984).

The term "cycloalkyl" refers to a mono- or polycyclic group which contains 3 to 15 carbons and may optionally contain one or two double bonds. Examples include cyclohexyl, adamantyl and norbornyl.

The term "aryl" refers to a mono- or polycyclic group which contains 6, 10, 12, or 14 carbons in which at least one ring is aromatic. Examples include phenyl, naphthyl and biphenyl.

The term "heteroaromatic" refers to a mono- or polycyclic group which contains 1 to 15 carbon atoms and from 1 to 4 heteroatoms, each of which is selected independently from a group including sulphur, nitrogen and oxygen, and which additionally contains from 1 to 3 five or six membered rings, at least one of which is aromatic.

The term "alpha-amino acid" refers to both the naturally occurring amino acids and other "non-protein" alpha-amino acids commonly utilized by those in the peptide chemistry arts when preparing synthetic analogues of naturally occurring peptides, including D and L forms. The naturally occurring amino acids are glycine, alanine, valine, leucine, isoleucine, serine, methionine, threonine, phenylalanine, tyrosine, tryptophan, cysteine, proline, histidine, aspartic acid, asparagine, glutamic acid, glutamine, y-carboxyglutamic acid, arginine, ornithine and lysine. Examples of "non-protein" alpha-amino acids include hydroxylysine, homoserine, homotyrosine, homophenylalanine, citrulline, kynurenine, 4-aminophenylalanine, 3-(2-naphthyl)-alanine, 3-(1-naphthyl)-alanine, methionine sulfone, t-butylalanine, t-butylglycine, 4-hydroxyphenyiglycine, aminoalanine, phenylglycine, vinylalanine, propargylalycine, 1,2,4-triazolo-3-alanine, 4,4,4-trifluorothreonine, thyronine, 6-hydroxytryptophan, 5-hydroxytryptophan, 3-hydroxykynurenine, 3-aminotyrosine, trifuoromethylalanine, 2-thienylalanine, (2-(4-pyridyl) ethyl)-cysteine, 3,4-dimethoxyphenylalanine, 3-(2-thiazolyl)-alanine, ibotenic acid, 1-amino-1-cyclopentanecarboxylic acid, 1-amino-1-cyclohexanecarboxylic dcid, quisqualic acid, 3-trifuoromethylphenylalanine, 4-trifuoromethylphenylalanine, cyclohexylalanine, cyclohexylglycine, thiohistidine, 3-methoxytyrosine, elastatinal, norleucine, norvaline, alloisoleucine, homoarginine, thioproline, dehydroproline, hydroxyproline, isonipectotic acid, homoserine, cyclohexylglycine, α-amino-n-butyric acid, cyclohexylalanine, aminophenyl-butyric acid, phenylalanines substituted at the ortho, meta, or para position of the phenyl moiety with one or two of the following: a $(C_1-C_4)$ alkyl, a $(C_1-C_4)$ alkoxy, halogen or nitro groups or substituted with a methylenedioxy group; β-2- and 3-thienyl-alanine, β-2- and 3-furanylalanine, β-2-, 3- and 4-pyridylalanine, β-(benzothienyl-2- and 3-yl) alanine, β-(1- and 2-naphthyl)alanine, O-alkylated derivatives of serine, threonine or tyrosine, S-alkylated cysteine, S-alkylated homocysteine, O-sulfate, O-phosphate and O-carboxylate esters of tyrosine, 3-sulfo-tyrosine, 3-carboxy-tyrosine, 3-phospho-tyrosine, 4-methane sulfonic acid ester of tyrosine, 4-methane phosphonic acid ester of tyrosine, 3,5-diiodotyrosine, 3-nitrotyrosine, ε-alkyl lysine, and delta-alkyl ornithine. Any of these alpha-amino acids may be substituted with a methyl group at the alpha position, a halogen at any aromatic residue on the alpha-amino side chain, or an appropriate protective group at the O, N, or S atoms of the side chain residues. Appropriate protective groups are disclosed in "Protective Groups In Organic Synthesis," T. W. Greene and P. G. M. Wurs, J. Wiley & Sons, NY, N.Y., 1991.

The term "bioisosteric replacement for $—CO_2H$" refers to group which may substitute for a carboxylic acid group in bioactive molecules. Examples of such groups are disclosed in Christopher A. Lipinski, "Bioisosteres in Drug Design" *Annual Reports In Medical Chemistry*, 21, pp. 286–88 (1986), and in C. W. Thornber, "Isosterism and Molecular Modification in Drug Design" *Chemical Society Reviews*, pp. 563–580. (1979)

The term "association" is used in reference to a condition of proximity between an inhibitor or portions thereof to an ICE molecule or portions thereof wherein the Juxtaposition is energetically favored by electrostatic or van der Waals interactions.

The term "hydrogen bond" refers to a favorable interaction that occurs whenever a suitable donor atom, X, bearing a proton, H, and a suitable acceptor atom, Y, have a separation of between 2.5 Å and 3.5 Å and where the angle X-H - - - Y is greater than 90 degrees. Suitable donor and acceptor atoms are well understood in medicinal chemistry [G. C. Pimentel and A. L. McClellan, The *Hydroaen Bond*, Freeman, San Francisco, 1960; R. Taylor and O. Kennard, "Hydrogen Bond Geometry in Organic Crystals", *Accounts of Chemical Research*, 17, pp. 320–326 (1984)].

The term "salt bridge" refers to the non-covalent attractive interaction between a positively charged moiety (P) and a negatively charged moiety (N) when the distance between the centers of mass of P and N is between 2 and 6 Angstroms. In calculating the center of mass, atoms which may contain a formal charge and atoms immediately adjacent to these are included. For example, a salt bridge may be formed between the positively charged guanidinium side chain of an arginine residue and the negative charged carboxylate side chain of a glutamate residue. Salt bridges are well understood in medicinal chemistry [L. Stryer, *Biochemistry*, Freeman, San Francisco, (1975); K. A. Dill, "Dominant Forces in Protein Folding", *Biochemistry*, 29, No. 31, pp. 7133–7155, (1990)].

The term "center of mass" refers to a point in three-dimensional space which represents a weighted average position of the masses that make up an object.

The terms "backbone chain" and "backbone" refer to the portion of a polypeptide which comprises the repeating unit —CO—CH —NH—.

The term "scaffold" refers to a structural building block which forms the basis of an ICE inhibitor according to this invention. Various moieties and functional groups are intended to be appended to the scaffold. The scaffolds of this invention are thus depicted having open valences. Various scaffolds of ICE inhibitors according to this invention include the portions:

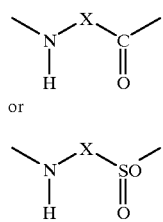

or

In those scaffolds, the NH and CO or $SO_2$ moieties represent a first and a second hydrogen bonding moiety, said moieties each being capable of forming a hydrogen bond with a backbone atom of ICE, said backbone atom being selected from the group consisting of the carbonyl oxygen of Arg-341, the amide —NH— of Arg-341, the carbonyl oxygen of Ser-339 and the amide —NH— of Ser-339.

The term "substitute" refers to the replacement of a hydrogen atom in a compound with a substituent group. In the present invention, those hydrogen atoms which form a part of a hydrogen bonding moiety which is capable of forming a hydrogen bond with the carbonyl oxygen of Arg-341 of ICE or the carbonyl oxygen of Ser-339 of ICE are excluded from substitution. These excluded hydrogen atoms include those which comprise an —NH— group which is alpha to a Z or a —CO— group and are depicted as —NH— rather than an X group or some other designation in the following diagrams: (a) through (t), (v), (rr) through (uu), (xx) through (zz), (aaa) through (ggg), and (I) through (VIID).

The term "straight chain" refers to a contiguous unbranching string of covalently bound members, i.e. atoms, which form a portion of a ring. The straight chain and the ring of which it forms a part may be substituted, but these substituents are not a part of the straight chain.

The term "$K_i$" refers to a numerical measure of the effectiveness of a compound in inhibiting the activity of a target enzyme such as ICE. Lower values of $K_i$ reflect higher effectiveness. The $K_i$ value is derived by fitting experimentally determined rate data to standard enzyme kinetic equations (see I. H. Segel, *Enzyme Kinetics*, Wiley-Interscience, 1975).

The term "minimize" refeLs to the systematic altering of the atomic geometry of a molecule or molecular complex so that any further minor perturbation of the atomic geometry would cause the total energy of the system as measured by a molecular mechanics force-field to increase. Minimization and molecular mechanics force-fields are well understood in computational chemistry [U. Burkert and N. L. Allinger, *Molecular Mechanics*, ACS Monograph 177, American Chemical Society, Washington, D.C. 1982 pages 59–78].

The term "strain energy" is used in this application to refer to the difference between the free conformation energy of a compound and the bound conformation energy of that compound when bound to ICE. The strain energy can be determined by the following steps: Evaluate the energy of the molecule when it has the conformation necessary for binding to ICE. Then minimize and reevaluate the energy—this is the free conformation energy. The strain energy for binding of a potential inhibitor to ICE is the difference between the free conformation energy and the bound conformation energy. In a preferred embodiment, the strain energy of an inhibitor of the present invention is less than about 10 kcal/mol.

The term "patient" as used in this application refers to any mammal, especially humans.

The term "pharmaceutically effective amount" refers to an amount effective in treating or ameliorating an IL-1 mediated disease in a patient. The term "prophylactically effective amount" refers to an amount effective in preventing or substantially lessening IL-1 mediated disease in a patient.

The term "pharmaceutically acceptable carrier or adjuvant" refers to a non-toxic carrier or adjuvant that may be administered to a patient, together with a compound of this invention, and which does not destroy the pharmacological activity thereof.

The term "pharmaceutically acceptable derivative" means any pharmaceutically acceptable salt, ester, or salt of such ester, of a compound of this invention or any other compound which, upon administration to a recipient, is capable of providing (directly or indirectly) a compound of this invention or an anti-ICE active metabolite or residue thereof.

Pharmaceutically acceptable salts of the compounds of this invention include, for example, those derived from pharmaceutically acceptable inorganic and organic acids and bases. Examples of suitable acids include hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, formic, benzoic, malonic, naphthalene-2-sulfonic and benzenesulfonic acids. Other acids, such as oxalic, while not in themselves pharmaceutically acceptable, may be employed in the preparation of salts useful as intermediates in obtaining the compounds of the invention and their pharmaceutically acceptable acid addition salts. Salts derived from appropriate bases include alkali metal (e.g., sodium), alkaline earth metal (e.g., magnesium), ammonium and N-($C_{1-4}$ alkyl)$_4^+$ salts.

This invention also envisions the "quaternization" of any basic nitrogen-containing groups of the compounds disclosed herein. The basic nitrogen can be quaternized with any agents known to those of ordinary skill in the art including, for example, lower alkyl halides, such as methyl, ethyl, propyl and butyl chloride, bromides and iodides; dialkyl sulfates including dimethyl, diethyl, dibutyl and diamyl sulfates; long chain halides such as decyl, lauryl, myristyl and stearyl chlorides, bromides and iodides; and aralkyl halides including benzyl and phenethyl bromides. Water or oil-soluble or dispersible products may be obtained by such quaternization.

The ICE inhibitors of this invention may contain one or more "asymmetric" carbon atoms and thus may occur as racemates and racemic mixtures, single enantiomers, diastereomeric mixtures and individual diastereomers. All such isomeric forms of these compounds are expressly included in the present invention. Each stereogenic carbon may be of the R or S configuration. Although specific compounds and scaffolds exemplified in this application may be depicted in a particular stereochemical configuration, compounds and scaffolds having either the opposite stereochemistry at any given chiral center or mixtures thereof are also envisioned.

Combinations of substituents and variables envisioned by this invention are only those that result in the formation of stable compounds. The term "stable", as used herein, refers to compounds which possess stability sufficient to allow manufacture and administration to a mammal by methods known in the art. Typically, such compounds are stable at a temperature of 40° C. or less, in the absence of moisture or other chemically reactive conditions, for at least a week.

DETAILED DESCRIPTION OF THE INVENTION

In order that the invention herein described may be more fully understood, the following detailed description is set forth.

We have discovered that compounds possessing the following novel combination of features are surprisingly effective ICE inhibitors:

a) a first and a second hydrogen bonding moiety, each of said moieties being capable of forming a hydrogen bond with a different backbone atom of ICE, said backbone atom being selected from the group consisting of the carbonyl oxygen of Arg-341, the amide —NH— group of Arg-341, the carbonyl oxygen of Ser-339 and the amide —NH— group of Ser-339;

b) a first and a second moderately hydrophobic moiety, said moieties each being capable of associating with a separate binding pocket of ICE when the inhibitor is bound thereto, said binding pocket being selected from the group consisting of the P2 binding pocket, the P3 binding pocket, the P4 binding pocket and the P' binding pocket; and c) an electronegative moiety comprising one or more electronegative atoms, said atoms being attached to the same atom or to adjacent atoms in the moiety and said moiety being capable of forming one or more hydrogen bonds or salt bridges with residues in the P1 binding pocket of ICE.

Preferably, any moderately hydrophobic moiety associating with the P2 binding pocket of ICE does so in such a way that:

a) the distance from the center of mass of the moderately hydrophobic moiety in the P2 binding pocket to the carbonyl oxygen of Arg-341 of ICE is between about 7.1 Å and about 12.5 Å;

b) the distance from the center of mass of the moderately hydrophobic moiety in the P2 binding pocket to the amide nitrogen of Arg-341 of ICE is between about 6.0 Å and about 12 Å; and c) the distance from the center of mass of the moderately hydrophobic moiety in the P2 binding pocket to the carbonyl oxygen of Ser-339 of ICE is between about 3.7 Å and about 9.5 Å.

Preferably, any moderately hydrophobic moiety associating with the P3 binding pocket of ICE does so in such a way that:

a) the distance from the center of mass of the moderately hydrophobic moiety in the P3 binding pocket to the carbonyl oxygen of Arg-341 of ICE is between about 3.9 Å and about 9.5 Å;

b) the distance from the center of mass of the moderately hydrophobic moiety in the P3 binding pocket to the amide nitrogen of Arg-341 of ICE is between about 5.4 Å and about 11 Å; and c) the distance from the center of mass of the moderately hydrophobic moiety in the P3 binding pocket to the carbonyl oxygen of Ser-339 of ICE is between about 7.0 Å and about 13 Å.

Preferably, any moderately hydrophobic moiety associating with the P4 binding pocket of ICE does so in such a way that:

a) the distance from the center of mass of the moderately hydrophobic moiety in the P4 binding pocket to the carbonyl oxygen of Arg-341 of ICE is between about 4.5 Å and about 7.5 Å;

b) the distance from the center of mass of the moderately hydrophobic moiety in the P4 binding pocket to the amide nitrogen of Arg-341 of ICE is between about 5.5 Å and about 8.5 Å; and c) the distance from the center of mass of the moderately hydrophobic moiety in the P4 binding pocket to the carbonyl oxygen of Ser-339 of ICE is between about 8 Å and about 11 Å.

Preferably, any moderately hydrophobic moiety associating with the P' binding pocket of ICE does so in such a way that:

a) the distance from the center of mass of the moderately hydrophobic moiety in the P' binding pocket to the carbonyl oxygen of Arg-341 of ICE is between about 11 Å and about 16 Å;

b) the distance from the center of mass of the moderately hydrophobic moiety in the P' binding pocket to the amide nitrogen of Arg-341 of ICE is between about 10 Å and about 15 Å; and c) the distance from the center of mass of the moderately hydrophobic moiety in the P'binding pocket to the carbonyl oxygen of Ser-339 of ICE is between about 8 Å and about 12 Å.

More preferably, all of the above associative conditions are met in the compounds of this invention. Preferably, the ICE inhibitor is characterized by a neutral or favorable enthalpic contribution from the sum of all electrostatic interactions between the inhibitor and ICE when the inhibitor is bound thereto.

Preferably, the ICE inhibitor further comprises less than two secondary amide bonds.

Preferably, the ICE inhibitor further comprises less than two groups selected from the set consisting of secondary amide groups and carbamate groups.

Preferably, when the inhibitor is bound to ICE, said moderately hydrophobic moieties separately associate with the P' binding pocket of ICE and the P2 binding pocket of ICE and the distance from the center of mass of the moderately hydrophobic moiety in the P' binding pocket to the center of mass of the moderately hydrophobic moiety in the P2 binding pocket is between about 6.5 Å and about 13 Å.

Preferably, when the inhibitor is bound to ICE, said inhibitor is bound to ICE, said moderately hydrophobic moieties separately associate with the P' binding pocket of ICE and the P3 binding pocket of ICE and the distance from the center of mass of the moderately hydrophobic moiety in the P' binding pocket to the center of mass of the moderately hydrophobic moiety in the P3 binding pocket is between about 6 Å and about 15 Å.

Preferably, when the inhibitor is bound to ICE, said inhibitor is bound to ICE, said moderately hydrophobic moieties separately associate with the P' binding pocket of ICE and the P4 binding pocket of ICE and the distance from the center of mass of the moderately hydrophobic moiety in the P' binding pocket to the center of mass of the moderately hydrophobic moiety in the P4 binding pocket is between about 14 Å and about 22 Å.

Preferably, when the inhibitor is bound to ICE, said moderately hydrophobic moieties separately associate with the P2 binding pocket of ICE and the P3 binding pocket of ICE and the distance from the center of mass of the moderately hydrophobic moiety in the P2 binding pocket to the center of mass of the moderately hydrophobic moiety in the P3 binding pocket is between about 5.5 Å and about 13 Å.

Preferably, when the inhibitor is bound to ICE, said moderately hydrophobic moieties separately associate with the P2 binding pocket of ICE and the P4 binding pocket of ICE and the distance from the center of mass of the moderately hydrophobic moiety in the P2 binding pocket to the center of mass of the moderately hydrophobic moiety in the P4 binding pocket is between about 9 Å and about 17 Å.

Preferably, when the inhibitor is bound to ICE, said moderately hydrophobic moieties separately associate with the P3 binding pocket of ICE and the P4 binding pocket of ICE and the distance from the center of mass of the moderately hydrophobic moiety in the P3 binding pocket to the center of mass of the moderately hydrophobic moiety in the P4 binding pocket is between about 7.5 Å and about 17 Å.

Preferably, when the inhibitor is bound to ICE, said first hydrogen bonding moiety forms a hydrogen bond with the carbonyl oxygen of Ser-339 of ICE and said second hydrogen bonding moiety forms a hydrogen bond with the carbonyl oxygen of Arg-341 of ICE and wherein the distance between said hydrogen bonding moieties is between about 5 Å and about 7.5 Å.

Preferably, when the inhibitor is bound to ICE, said first hydrogen bonding moiety forms a hydrogen bond with the carbonyl oxygen of Ser-339 of ICE and said second hydrogen bonding moiety forms a hydrogen bond with the amide —NH— group of Arg-341 of ICE and wherein the distance between said moieties is between about 2.5 Å and about 5 Å.

Preferably, when the inhibitor is bound to ICE, said first hydrogen bonding moiety forms a hydrogen bond with the carbonyl oxygen of Arg-341 of ICE and said second hydrogen bonding moiety forms a hydrogen bond with the amide —NH— group of Arg-341 of ICE and wherein the distance between said hydrogen bonding moieties is between about 2.5 Å and about 4 Å.

The practitioner skilled in the art will appreciate that there are a number of means to design the inhibitors of the present invention. These same means may be used to select a candidate compound for screening as an ICE inhibitor. This design or selection may begin with selection of the various moieties which fill binding pockets.

There are a number of ways to select moieties to fill individual binding pockets. These include visual inspection of a physical model or computer model of the active site and manual docking of models of selected moieties into various binding pockets. Modeling software that is well known and available in the art may be used. These include QUANTA [Molecular Simulations, Inc., Burlington, Mass., 1992], SYBYL [Molecular Modeling Software, Tripos Associates, Inc., St. Louis, Mo., 1992], AMBER [S. J. Weiner, P. A. Kollman, D. A. Case, U. C. Singh, C. Ghio, G. Alagona, and P. Weiner, *J. Am. Chem. Soc.*, vol. 106, pp. 765–784 (1984)], or CHARMM [B. R. Brooks, R. E. Bruccoleri, B. D. Olafson, D. J. States, S Swaminathan, and M. Karplus, *J. Comp. Chem.* vol. 4, pp. 187–217 (1983)]. This modelling step may be followed by energy minimization with standard molecular mechanics forcefields such as CHARMM and AMBER. In addition, there are a number of more specialized computer programs to assist in the process of selecting the binding moieties of this invention. These include:

1. GRID (Goodford, P. J. A Computational Procedure for Determining Energetically Favorable Binding Sites on Biologically Important Macromolecules. *J. Med. Chem.* 1985, 28, 849–857). GRID is available from Oxford University, Oxford, UK.
2. MCSS (Miranker, A.; Karplus, M. Functionality Maps of Binding Sites: A Multiple Copy Simultaneous Search Method. *Proteins: Structure. Function and Genetics* 1991, 11, 29–34). MCSS is available from Molecular Simulations, Burlington, Mass.
3. AUTODOCK (Goodsell, D. S.; Olsen, A. J. Automated Docking of Substrates to Proteins by Simmulated Annealing. *PROTEINS: Structure, Function and Genetics* 1990, 8, 195–202). AUTODOCK is available from the Scripps Research Institute, La Jolla, Calif.
4. DOCK (Kuntz, I. D.; Blaney, J. M.; Oatley, S. J.; Langridge, R.; Ferrin, T. E. A Geometric Approach to Macromolecule-Ligand Interactions. *J. Mol. Biol.* 1982, 161, 269–288). DOCK is available from the University of California, San Francisco, Calif.

Once suitable binding moieties have been selected, they can be assembled into a single inhibitor. This assembly may be accomplished by connecting the various moieties to a central scaffold. The assembly process may, for example, be done by visual inspection followed by manual model building, again using software such as Quanta or Sybyl. A number of other programs may also be used to help select ways to connect the various moieties. These include:

1. CAVEAT (Bartlett, P. A.; Shea, G. T.; Telfer, S. J.; Waterman, S. CAVEAT: A Program to Facilitate the Structure-Derived Design of Biologically Active Molecules. In "Molecular Recognition in Chemical and Biological Problems," Special Pub., Royal Chem. Soc. 1989, 78, 182–196). CAVEAT is available from the University of California, Berkeley, Calif.
2. 3D Database systems such as MACCS-3D (MDL Information Systems, San Leandro, Calif.). This area has been recently reviewed by Martin (Martin, Y. C. 3D Database Searching in Drug Design. *J. Med. Chem.* 1992, 35, 2145–2154).
3. HOOK (available from Molecular Simulations, Burlington, Mass.)

In addition to the above computer assisted modeling of inhibitor compounds, the inhibitors of this invention may be constructed "de novo" using either an empty active site or optionally including some portions of a known inhibitor. Such methods are well known in the art. They include, for example:

1. LUDI (Bohm, H. J. The Computer Program LUDI: A New Method for the De Novo Design of Enzyme Inhibitors. *J. Comp. Aid. Molec. Design.* 1992, 6, 61–78). LUDI is available from Biosym Technologies, San Diego, Calif.

2. LEGEND (Nishibata, Y., Itai, A., *Tetrahedron*, 47 (1991) 8985). LEGEND is available from Molecular Simultations, Burlington, Mass.

3. LeapFrog (available from Tripos associates, St. Louis, Mo.)

A number of techniques commonly used for modeling drugs may be employed (For a review, see: Cohen, N. C.; Blaney, J. M.; Humblet, C.; Gund, P.; Barry, D. C., "Molecular Modeling Software and Methods for Medicinal Chemistry", *J. Med. Chem.*, 33, pp. 883–894 (1990)). There are likewise a number of examples in the chemical literature of techniques that can be applied to specific drug design projects. For a review, see: Navia, M. A. and Murcko, M. A., "The Use of Structural Information in Drug Design", *Current Opinions in Structural Biology*, 2, pp. 202–210 (1992). Some examples of these specific applications include: Baldwin, J. J. et al., "Thienothiopyran-2-sulfonamides: Novel Topically Active Carbonic Anhydrase Inhibitors for the Treatment of Glaucoma", *J. Med. Chem.*, 32, pp. 2510–2513 (1989); Appelt, K. et al., "Design of Enzyme Inhibitors Using Iterative Protein Crystallographic Analysis", *J. Med. Chem.*, 34, pp. 1925–1934 (1991); and Ealick, S. E. et al., "Application of Crystallographic and Modeling Methods in the Design of Purine Nucleotide Phosphorylase Inhibitors" *Proc. Nat. Acad. Sci. USA*, 88, pp. 11540–11544 (1991).

Using the novel combination of steps of the present invention, the skilled artisan can advantageously avoid time consuming and expensive experimentation to determine enzymatic inhibition activity of particular compounds. The method also is useful to facilitate rational design of ICE inhibitors and therapeutic and prophylactic agents against IL-1-mediated diseases. Accordingly, the present invention relates to such inhibitors.

A variety of conventional techniques may be used to carry out each of the above evaluations as well as the evaluations necessary in screening a candidate compound for ICE inhibiting activity. Generally, these techniques involve determining the location and binding proximity of a given moiety, the occupied space ot a bound inhibitor, the deformation energy of binding of a given compound and electrostatic interaction energies. Examples of conventional techniques useful in the above evaluations include: quantum mechanics, molecular mechanics, molecular dynamics, Monte Carlo sampling, systematic searches and distance geometry methods [G. R. Marshall, *Ann. Ref. Pharmacol. Toxicol.*, 27, p. 193 (1987)]. Specific computer software has been developed for use in carrying out these methods. Examples of programs designed for such uses include: Gaussian 92, revision E.2 [M. J. Frisch, Gaussian, Inc., Pittsburgh, Pa. ©1993]; AMBER, version 4.0 [P. A. Kollman, University of California at San Francisco, ©1993]; QUANTA/CHARMM [Molecular Simulations, Inc., Burlington, Mass. @1992]; and Insight II/Discover [Biosysm Technologies Inc., San Diego, Calif. ©1992]. These programs may be implemented, for instance, using a Silicon Graphics Indigo2 workstation or IBM RISC/6000 workstation model 550. Other hardware systems and software packages will be known and of evident applicability to those skilled in the art.

Different classes of active ICE inhibitors, according to this invention, may interact in similar ways with the various binding pockets of the ICE active site. The spatial arrangement of these important groups is often referred to as a pharmacophore. The concept of the pharmacophore has been well described in the literature [D. Mayer, C. B. Naylor, I. Motoc, and G. R. Marshall, *J. Comp. Aided Molec. Design* vol. 1, pp. 3–16 (1987); A. Hopfinger and B. J. Burke, in *Concepts and Applications of Molecular Similarity*, M. A. Johnson and G. M. Maggiora, ed., Wiley (1990).]

Different classes of ICE inhibitors of this invention may also use different scaffolds or core structures, but all of these cores will allow the necessary moieties to be placed in the active site such that the specific interactions necessary for binding may be obtained. These compounds are best defined in terms of their ability to match the pharmacophore, i.e., their structural identity relative to the shape and properties of the active site of ICE.

The ICE inhibitors of one embodiment of this invention comprise a first and a second hydrogen bonding moiety, a first and a second moderately hydrophobic moiety, and an electronegative moiety which comprise or are covalently bound to one of the following scaffolds:

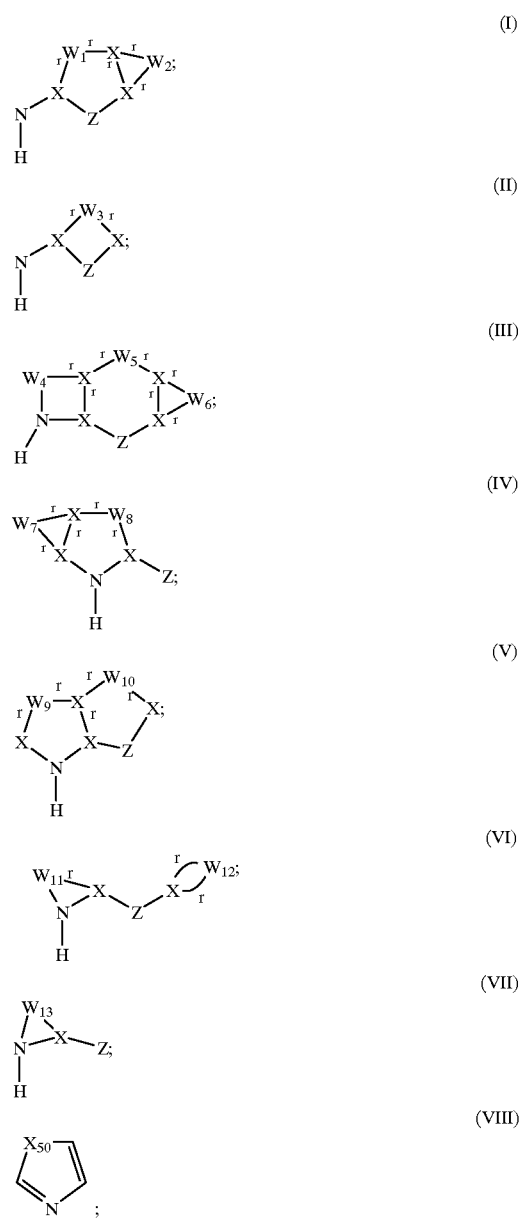

-continued

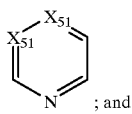
(IX)

(X)

Specifically, this embodiment includes:
An ICE inhibitor comprising:
a) a scaffold of formula I:

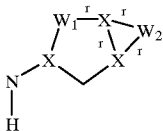
(I)

wherein:
each X is independently C or N;
Z is CO or $SO_2$;
$W_1$ is a straight chain comprising 1–3 covalently bound members independently selected from the group consisting of C, N, S and O, said covalent bonds between said members being independently saturated or unsaturated and said chain comprising two ends which are covalently bound to two different X atoms through bonds r;
$W_2$ is a straight chain comprising 3–5 covalently bound members independently selected from the group consisting of C, N, S and O, said covalent bonds between said members being independently saturated or unsaturated and said chain comprising two ends which are covalently bound to two different X atoms through bonds r;
each bond labeled r is independently a single or a double bond;
H is a first hydrogen bonding moiety and Z is a second hydrogen bonding moiety, each of said moieties being capable of forming a hydrogen bond with a different backbone atom of ICE, said backbone atom being selected from the group consisting of the carbonyl oxygen of Arg-341, the amide —NH— group of Arg-341, the carbonyl oxygen of Ser-339 and the amide —NH— group of Ser-339;
b) a first and a second moderately hydrophobic moiety, said moieties each being covalently bound to said scaffold and each being capable of associating with a separate binding pocket of ICE when the inhibitor is bound thereto, said binding pocket being selected from the group consisting of the P2 binding pocket, the P3 binding pocket, the P4 binding pocket and the P' binding pocket; and
c) an electronegative moiety comprising one or more electronegative atoms, said atoms being attached to the same atom or to adjacent atoms in the moiety and said moiety being covalently bound to said scaffold and being capable of forming one or more hydrogen bonds or salt bridges with residues in the P1 binding pocket of ICE.

Preferably, the scaffold has the formula:

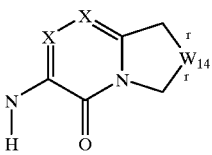
(IA)

wherein:
each X is independently C or N;
$W_{14}$ is a straight chain comprising 1–3 covalently bound members independently selected from the group consisting of C, N, S and O, said covalent bonds between said members being independently saturated or unsaturated and said chain comprising two ends which are covalently bound to two different C atoms through bonds r; and
each bond labeled r is independently a single or a double bond.

Alternatively, the scaffold has the formula:

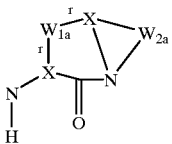
(IB)

wherein:
X is C or N;
$W_{1a}$ is a straight chain comprising 1–3 covalently bound members independently selected from the group consisting of C, N, S and O, said covalent bonds between said members being independently saturated or unsaturated and said chain comprising two ends which are covalently bound to two different X atoms through bonds r;
$W_{2a}$ is a straight chain comprising 3–4 covalently bound members independently selected from the group consisting of C, N, S and O, said chain comprising two ends which are covalently bound to two different atoms to form an aryl or heteroaromatic ring therewith; and
each bond labeled r is independently a single or a double bond.

Alternatively, the scaffold has the formula:

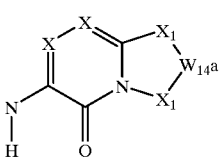
(IC)

wherein:
each X is independently C or N;
each $X_1$ is independently C, N, or O; and
$W_{14a}$ is a straight chain comprising 1–3 covalently bound members independently selected from the group consisting of C, N, S and O, said covalent bonds between said members being saturated or unsaturated and said chain comprising two ends which are covalently bound to two different $X_1$ atoms to form a non-aromatic ring therewith.

An ICE inhibitor comprising:
a) a scaffold of formula II:

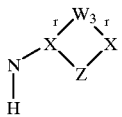

(II)

wherein:
- each X is independently C or N;
- Z is CO or $SO_2$;
- $W_3$ is a straight chain comprising 2–4 covalently bound members independently selected from the group consisting of C, N, S and O, said covalent bonds between said members being independently saturated or unsaturated and said chain comprising two ends which are covalently bound to two different X atoms through bonds r;
- each bond labeled r is independently a single or a double bond;
- H is a first hydrogen bonding moiety and Z is a second hydrogen bonding moiety, each of said moieties being capable of forming a hydrogen bond with a different backbone atom of ICE, said backbone atom being selected from the group consisting of the carbonyl oxygen of Arg-341, the amide —NH— group of Arg-341, the carbonyl oxygen of Ser-339 and the amide —NH— group of Ser-339;

b) a first and a second moderately hydrophobic moiety, said moieties each being covalently bound to said scaffold and each being capable of associating with a separate binding pocket of ICE when the inhibitor is bound thereto, said binding pocket being selected from the group consisting of the P2 binding pocket, the P3 binding pocket, the P4 binding pocket and the P' binding pocket; and c) an electronegative moiety comprising one or more electronegative atoms, said atoms being attached to the same atom or to adjacent atoms in the moiety and said moiety being covalently bound to said scaffold and being capable of forming one or more hydrogen bonds or salt bridges with residues in the P1 binding pocket of ICE.

Preferably, the scaffold has the formula:

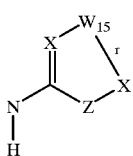

(IIA)

wherein:
- each X is independently C or N;
- Z is CO or $SO_2$;
- $W_{15}$ is a straight chain comprising 1–2 covalently bound members independently selected from the group consisting of C, N, S and O, said covalent bonds between said members being independently saturated or unsaturated and said chain comprising two ends which are covalently bound to two different X atoms; and the bond labeled r is a single or a double bond.

Alternatively, the scaffold has the formula:

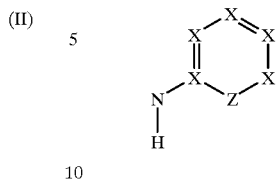

(IIB)

wherein:
- each X is independently C or N; and
- Z is CO or $SO_2$.

Alternatively, the scaffold has the formula:

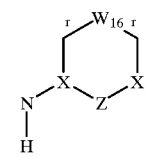

(IIC)

wherein:
- each X is independently C or N;
- Z is CO or $SO_2$;
- $W_{16}$ is a straight chain comprising 1–2 covalently bound members independently selected from the group consisting of C, N, S and O, said covalent bonds between said members being independently saturated or unsaturated and said chain comprising two ends which are covalently bound to two different C atoms through bonds r; and
- each bond labeled r is independently a single or a double bond.

An ICE inhibitor comprising:
a) a scaffold of formula III:

(III)

wherein:
- each X is independently C or N;
- Z is CO or $SO_2$;
- $W_4$ is a straight chain comprising 2–4 covalently bound members independently selected from the group consisting of C, N, S and O, said covalent bonds between said members being independently saturated or unsaturated and said chain comprising two ends which are covalently bound to two different atoms;
- $W_5$ is a direct bond or a straight chain comprising 1–2 covalently bound members independently selected from the group consisting of C, N, S and O, said covalent bonds between said members being independently saturated or unsaturated and said chain comprising two ends which are covalently bound to two different X atoms through bonds r;
- $W_6$ is a straight chain comprising 3–5 covalently bound members independently selected from the group consisting of C, N, S and O, said covalent bonds between said members being independently saturated or unsaturated and said chain comprising two ends which are covalently bound to two different X atoms through bonds r;

each bond labeled r is independently a single or a double bond;

H is a first hydrogen bonding moiety and Z is a second hydrogen bonding moiety, each of said moieties being capable of forming a hydrogen bond with a different backbone atom of ICE, said backbone atom being selected from the group consisting of the carbonyl oxygen of Arg-341, the amide —NH— group of Arg-341, the carbonyl oxygen of Ser-339 and the amide —NH— group of Ser-339;

b) a first and a second moderately hydrophobic moiety, said moieties each being covalently bound to said scaffold and each being capable of associating with a separate binding pocket of ICE when the inhibitor is bound thereto, said binding pocket being selected from the group consisting of the P2 binding pocket, the P3 binding pocket, the P4 binding pocket and the P' binding pocket; and c) an electronegative moiety comprising one or more electronegative atoms, said atoms being attached to the same atom or to adjacent atoms in the moiety and said moiety being covalently bound to said scaffold and being capable of forming one or more hydrogen bonds or salt bridges with residues in the P1 binding pocket of ICE.

Preferably, the scaffold has the formula:

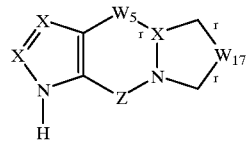

(IIIA)

wherein:

each X is independently C or N;

Z is CO or $SO_2$;

$W_5$ is a direct bond or a straight chain comprising 1–2 covalently bound members independently selected from the group consisting of C, N, S and O, said covalent bonds between said members being independently saturated or unsaturated and said chain comprising two ends which are covalently bound to two different atoms;

$W_{17}$ is a straight chain comprising 1–3 covalently bound members independently selected from the group consisting of C, N, S and O, said covalent bonds between said members being independently saturated or unsaturated and said chain comprising two ends which are covalently bound to two different C atoms through bonds r; and each bond labeled r is independently a single or a double bond.

Alternatively, the scaffold has the formula:

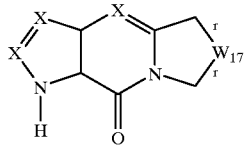

(IIIB)

wherein:

each X is independently C or N;

$W_{17}$ is a straight chain comprising 1–3 covalently bound members independently selected from the group consisting of C, N, S and O, said covalent bonds between said members being independently saturated or unsaturated and said chain comprising two ends which are covalently bound to two different C atoms through bonds r; and each bond labeled r is independently a single or a double bond.

An ICE inhibitor comprising:

a) a scaffold of formula IV:

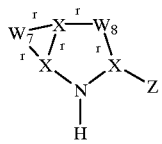

(IV)

wherein:

each X is independently C or N;

Z is CO or $SO_2$;

$W_7$ is a straight chain comprising 3–5 covalently bound members independently selected from the group consisting of C, N, S and O, said covalent bonds between said members being independently saturated or unsaturated and said chain comprising two ends which are covalently bound to two different X atoms through bonds r;

$W_8$ is a straight chain comprising 1–3 covalently bound members independently selected from the group consisting of C, N, S and O, said covalent bonds between said members being independently saturated or unsaturated, and said chain comprising two ends which are covalently bound to two different X atoms through bonds r;

each bond labeled r is independently a single or a double bond;

H is a first hydrogen bonding moiety and Z is a second hydrogen bonding moiety, each of said moieties being capable of forming a hydrogen bond with a different backbone atom of ICE, said backbone atom being selected from the group consisting of the carbonyl oxygen of Arg-341, the amide —NH— group of Arg-341, the carbonyl oxygen of Ser-339 and the amide —NH— group of Ser-339;

b) a first and a second moderately hydrophobic moiety, said moieties each being covalently bound to said scaffold and each being capable of associating with a separate binding pocket of ICE when the inhibitor is bound thereto, said binding pocket being selected from the group consisting of the P2 binding pocket, the P3 binding pocket, the P4 binding pocket and the P' binding pocket; and c) an electronegative moiety comprising one or more electronegative atoms, said atoms being attached to the same atom or to adjacent atoms in the moiety and said moiety being covalently bound to said scaffold and being capable of forming one or more hydrogen bonds or salt bridges with residues in the P1 binding pocket of ICE.

Preferably, the scaffold has the formula:

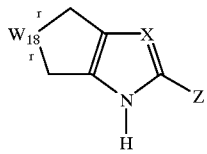

(IVA)

wherein:
each X is independently C or N;
Z is CO or $SO_2$;
$W_{18}$ is a straight chain comprising 1–3 covalently bound members independently selected from the group consisting of C, N, S and O, said covalent bonds between said members being independently saturated or unsaturated and said chain comprising two ends which are covalently bound to two different C atoms through bonds r; and
each bond labeled r is independently a single or a double bond.

Alternatively, the scaffold has the formula:

(IVB)

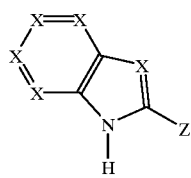

wherein:
each X is independently C or N; and
Z is CO or $SO_2$.

Alternatively, the scaffold has the formula:

(IVC)

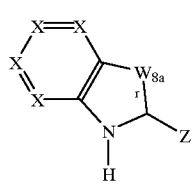

wherein:
each X is independently C or N;
Z is CO or $SO_2$;
$W_{8a}$ is a straight chain comprising 1–3 covalently bound members independently selected from the group consisting of C, N, S and O, said covalent bonds between said members being independently saturated or unsaturated and said chain comprising two ends which are covalently bound to two different C atoms; and the bond labeled r is a single or a double bond.

Alternatively, the scaffold has the formula:

(IVD)

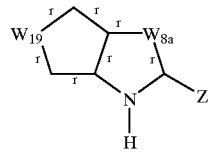

wherein:

Z is CO or $SO_2$;

$W_{8a}$ is a straight chain comprising 1–3 covalently bound members independently selected from the group consisting of C, N, S and O, said covalent bonds between said members being independently saturated or unsaturated and said chain comprising two ends which are covalently bound to two different C atoms through bonds r;

$W_{19}$ is a straight chain comprising 1–3 covalently bound members independently selected from the group consisting of C, N, S and O, said covalent bonds between said members being independently saturated or unsaturated and said chain comprising two ends which are covalently bound to two different C atoms through bonds r; and each bond labeled r is independently a single or a double bond.

Alternatively, the scaffold has the formula:

(IVE)

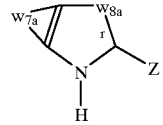

wherein:

Z is CO or $SO_2$;

$W_{8a}$ is a straight chain comprising 1–3 covalently bound members independently selected from the group consisting of C, N, S and O, said covalent bonds between said members being independently saturated or unsaturated and said chain comprising two ends which are covalently bound to two different C atoms;

$W_{7a}$ is a straight chain comprising 3 covalently bound members independently selected from the group consisting of C, N, S and O, said chain comprising two ends which are covalently bound to two different C atoms to form an aryl ring therewith; and the bond labeled r is a single or a double bond.

An ICE inhibitor comprising:

a) a scaffold of formula V:

wherein:

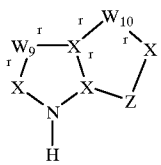
(V)

each X is independently C or N;
Z is CO or SO$_2$;
W$_9$ is a straight chain comprising 1–3 covalently bound members independently selected from the group consisting of C, N, S and O, said covalent bonds between said members being independently saturated or unsaturated and said chain comprising two ends which are covalently bound to two different X atoms through bonds r;
W$_{10}$ is a straight chain comprising 1–3 covalently bound members independently selected from the group consisting of C, N, S and O, said covalent bonds between said members being independently saturated or unsaturated and said chain comprising two ends which are covalently bound to two different X atoms through bonds r;
each bond labeled r is independently a single or a double bond;
H is a first hydrogen bonding moiety and Z is a second hydrogen bonding moiety, each of said moieties being capable of forming a hydrogen bond with a different backbone atom of ICE, said backbone atom being selected from the group consisting of the carbonyl oxygen of Arg-341, the amide —NH— group of Arg-341, the carbonyl oxygen of Ser-339 and the amide —NH— group of Ser-339;
b) a first and a second moderately hydrophobic moiety, said moieties each being covalently bound to said scaffold and each being capable of associating with a separate binding pocket of ICE when the inhibitor is bound thereto, said binding pocket being selected from the group consisting of the P2 binding pocket, the P3 binding pocket, the P4 binding pocket and the P' binding pocket; and
c) an electronegative moiety comprising one or more electronegative atoms, said atoms being attached to the same atom or to adjacent atoms in the moiety and said moiety being covalently bound to said scaffold and being capable of forming one or more hydrogen bonds or salt bridges with residues in the P1 binding pocket of ICE.

Preferably, the scaffold has the formula:

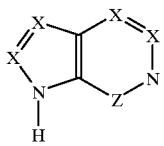
(VA)

wherein:
each X is independently C or N; and
Z is CO or SO$_2$.

Alternatively, the scaffold has the formula:

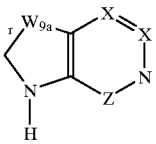
(VB)

wherein:
each X is independently C or N;
Z is CO or SO$_2$;
W$_{9a}$ is a straight chain comprising 1–3 covalently bound members independently selected from the group consisting of C, N, S and O, said covalent bonds between said members being independently saturated or unsaturated and said chain comprising two ends which are covalently bound to two different C atoms; and
the bond labeled r is a single or a double bond.

Alternatively, the scaffold has the formula:

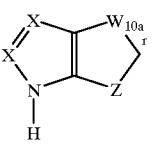
(VC)

wherein:
each X is independently C or N;
Z is CO or SO$_2$;
W$_{10a}$ is a straight chain comprising 1–3 covalently bound members independently selected from the group consisting of C, N, S and O, said covalent bonds between said members being independently saturated or unsaturated and said chain comprising two ends which are covalently bound to two different X atoms; and
the bond labeled r is a single or a double bond.

An ICE inhibitor comprising:
a) a scaffold of formula VI:

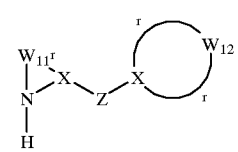
(VI)

wherein:
each X is independently C or N;
Z is CO or SO$_2$;
W$_{11}$ is a straight chain comprising 3–5 covalently bound members independently selected from the group consisting of C, N, S and O, said covalent bonds between said members being independently saturated or unsaturated and said chain comprising two ends which are covalently bound to two different atoms to form a ring which may optionally be benzofused or pyridinofused;
W$_{12}$ is a straight chain comprising 4–6 covalently bound members independently selected from the group consisting of C, N, S and O, said covalent bonds between said members being independently saturated or unsaturated and said chain comprising two ends which are covalently bound to the indicated X atom through bonds r;

each bond labeled r is independently a single or a double bond;

H is a first hydrogen bonding moiety and Z is a second hydrogen bonding moiety, each of said moieties being capable of forming a hydrogen bond with a different backbone atom of ICE, said backbone atom being selected from the group consisting of the carbonyl oxygen of Arg-341, the amide —NH— group of Arg-341, the carbonyl oxygen of Ser-339 and the amide —NH— group of Ser-339;

b) a first and a second moderately hydrophobic moiety, said moieties each being covalently bound to said scaffold and each being capable of associating with a separate binding pocket of ICE when the inhibitor is bound thereto, said binding pocket being selected from the group consisting of the P2 binding pocket, the P3 binding pocket, the P4 binding pocket and the P' binding pocket; and c) an electronegative moiety comprising one or more electronegative atoms, said atoms being attached to the same atom or to adjacent atoms in the moiety and said moiety being covalently bound to said scaffold and being capable of forming one or more hydrogen bonds or salt bridges with residues in the P' binding pocket of ICE.

Preferably, the scaffold has the formula:

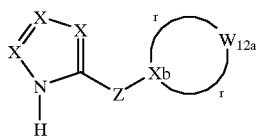

(VIA)

wherein:

each X and $X_b$ is independently C or N;

Z is CO or $SO_2$;

$W_{12a}$ is a straight chain comprising 4–6 covalently bound members independently selected from the group consisting of C, N, S and O, said covalent bonds between said members being independently saturated or unsaturated and said chain comprising two ends which are covalently bound to the indicated $X_b$ atom through bonds r; and each bond labeled r is independently a single or a double bond.

Alternatively, the scaffold has the formula:

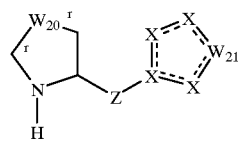

(VIB)

wherein:

each X is independently C or N;

Z is CO or $SO_2$;

$W_{20}$ is a straight chain comprising 1–3 covalently bound members independently selected from the group consisting of C, N, S and O, said covalent bonds between said members being independently saturated or unsaturated and said chain comprising two ends which are covalently bound to two different C atoms through bonds r;

$W_{21}$ is a straight chain comprising 1–2 covalently bound members independently selected from the group consisting of C, N, S and O, said chain comprising two ends which are covalently bound to two different C atoms to form an aryl ring therewith; and each bond labeled r is independently a single or a double bond.

An ICE inhibitor comprising:

(a) a scaffold of formula VII:

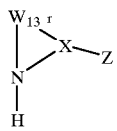

(VII)

wherein:

X is C or N;

Z is CO or $SO_2$;

$W_{13}$ is a straight chain comprising 3–5 covalently bound members independently selected from the group consisting of C, N, S and O, said covalent bonds between said members being independently saturated or unsaturated and said chain comprising two ends which are covalently bound to two different atoms;

the bond labeled r is a single or a double bond;

H is a first hydrogen bonding moiety and Z is a second hydrogen bonding moiety, each of said moieties being capable of forming a hydrogen bond with a different backbone atom of ICE, said backbone atom being selected from the group consisting of the carbonyl oxygen of Arg-341, the amide —NH— group of Arg-341, the carbonyl oxygen of Ser-339 and the amide —NH— group of Ser-339;

b) a first and a second moderately hydrophobic moiety, said moieties each being covalently bound to said scaffold and each being capable of associating with a separate binding pocket of ICE when the inhibitor is bound thereto, said binding pocket being selected from the group consisting of the P2 binding pocket, the P3 binding pocket, the P4 binding pocket and the P' binding pocket; and c) an electronegative moiety comprising one or more electronegative atoms, said atoms being attached to the same atom or to adjacent atoms in the moiety and said moiety being covalently bound to said scaffold and being capable of forming one or more hydrogen bonds or salt bridges with residues in the P1 binding pocket of ICE.

Preferably, the scaffold has the formula:

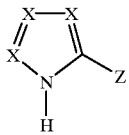
(VIIA)

wherein:
each X is independently C or N; and
Z is CO or SO$_2$.

Alternatively, the scaffold has the formula:

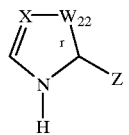
(VIIB)

wherein:
X is C or N;
Z is CO or SO$_2$;
W$_{22}$ is a straight chain comprising 1–3 covalently bound members independently selected from the group consisting of C, N, S and O, said covalent bonds between said members being independently saturated or unsaturated and said chain comprising two ends which are covalently bound to two different atoms; and
the bond labeled r is a single or a double bond.

Alternatively, the scaffold has the formula:

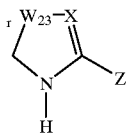
(VIIC)

wherein:
X is C or N;
Z is CO or SO$_2$;
W$_{23}$ is a straight chain comprising 1–3 covalently bound members independently selected from the group consisting of C, N, S and O, said covalent bonds between said members being independently saturated or unsaturated and said chain comprising two ends which are covalently bound to two different atoms; and
the bond labeled r is a single or a double bond.

Alternatively, the scaffold has the formula:

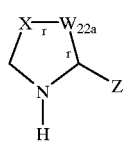
(VIID)

wherein:
X is C or N;
Z is CO or SO$_2$;
W$_{22a}$ is a straight chain comprising 1–3 covalently bound members independently selected from the group consisting of C, N, S and O, said covalent bonds between said members being independently saturated or unsaturated and said chain comprising two ends which are covalently bound to two different atoms through bonds r; and
each bond labeled r is independently a single or a double bond.

The ICE inhibitors of another embodiment of this invention comprise:

a) a scaffold comprising any monocyclic, bicyclic or tricyclic system, wherein each ring of said system comprises 5–7 members, said system comprising C, N, O or S, said system being aromatic or non-aromatic and comprising a central ring, wherein the distance between the centroid of said central ring and the alpha carbon of Cys-285 of ICE is between about 5.0 Å and about 6.0 Å when the inhibitor is bound to ICE and the distance between the centroid of said central ring and the alpha carbon of His-237 of ICE is between about 5.5 Å and about 6.5 Å when the inhibitor is bound to ICE;

b) a first hydrogen bonding moiety and a second hydrogen bonding moiety, each of said moieties being capable of forming a hydrogen bond with a different backbone atom of ICE, said atoms being selected from the group consisting of the carbonyl oxygen of Arg-341, the amide —NH— group of Arg-341, the carbonyl oxygen of Ser-339 and the amide —NH— group of Ser-339;

c) a first and a second moderately hydrophobic moiety, said moieties each being covalently bound to said scaffold and each being capable of associating with a separate binding pocket of ICE when the inhibitor is bound thereto, said binding pocket being selected from the group consisting of the P2 binding pocket, the P3 binding pocket, the P4 binding pocket and the P' binding pocket; and d) an electronegative moiety comprising one or more electronegative atoms, said atoms being attached to the same atom or to adjacent atoms in the moiety and said moiety being covalently bound to said scaffold and being capable of forming one or more hydrogen bonds or salt bridges with residues in the P1 binding pocket of ICE.

Preferably, the central ring has the formula (VIII), as defined above, and X$_{50}$ is S, O or N.

Alternatively, the central ring has the formula (IX), as defined above, and X$_{51}$ is independently C or N.

Alternatively, central ring has the formula (X), as defined above, $$Z_{50} \text{ is } C{=}O, \ S{=}O, \text{ or } C{=}S; \text{ and}$$

the bond labeled rr is a single or a double bond.

The ICE inhibitors of another embodiment of this invention are those of formulas:

wherein:

X₁ is CH or N;

g is 0 or 1;

each J is independently selected from the group consisting of —H, —OH, and —F, provided that when a first and second J are bound to a C and said first J is —OH, said second J is —H;

m is 0, 1, or 2;

T is —Ar₃, —OH, —CF₃, —CO—CO₂H, —CO₂H or any bioisosteric replacement for —CO₂H;

R₁ is selected from the group consisting of the following formulae, in which any ring may optionally be singly or multiply substituted at any carbon by Q₁ at any nitrogen by R₅, or at any atom by =O, —OH, —CO₂H, or halogen, and in which any saturated ring may optionally be unsaturated at one or two bonds:

(m) 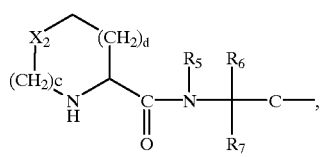
(n) 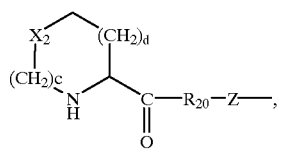
(o) 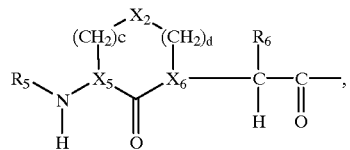
(p) 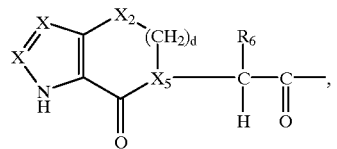
(q) 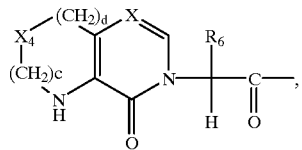
(r) 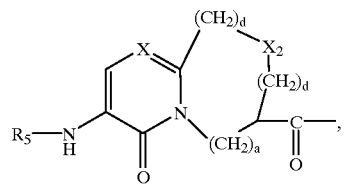
(s) 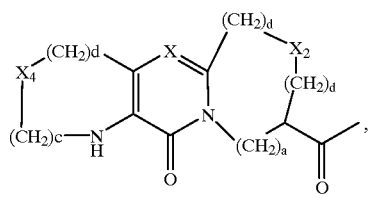
(t) 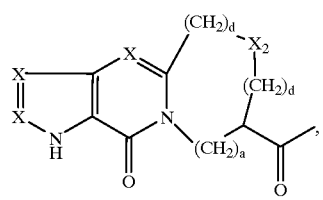
(v) 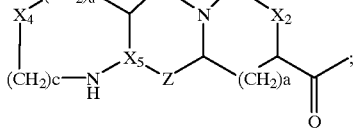
$R_{20}$ is selected from the group consisting of:
(aa1) 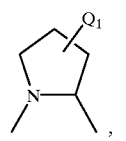
(aa2) 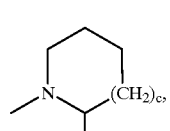
(aa3) 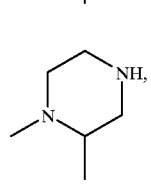
(aa4) 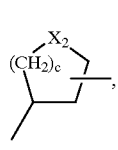
(aa5) 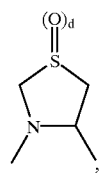
(bb) 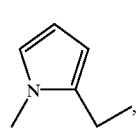
(cc) 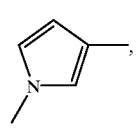
(dd) 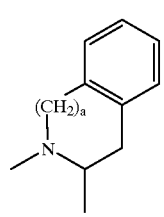

-continued (ee) 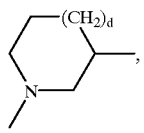

(ff) 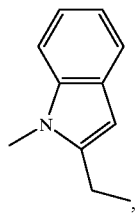

(gg) 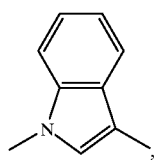

(gga) 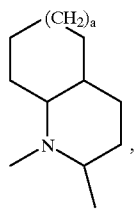

(ggb) 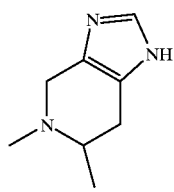

, and (ggc) 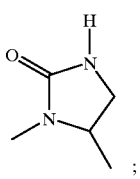
;

wherein each ring C is independently chosen from the group consisting of benzo, pyrido, thieno, pyrrolo, furano, thiazolo, isothiazolo, oxazolo, isoxazolo, pyrimido, imidazolo, cyclopentyl, and cyclohexyl;

$R_3$ is
—CN,
—CH=CH—$R_9$,
—CH=N—O—$R_9$,
—(CH$_2$)$_{1-3}$—T$_1$—$R_9$,
—CJ$_2$—$R_9$,
—CO—$R_{13}$, or

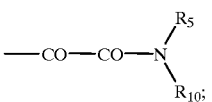

each $R_4$ is independently selected from the group consisting of:
—H,
—Ar$_1$,
—$R_9$,
—T$_1$—$R_9$, and
—(CH$_2$)$_{1,2,3}$—T$_1$—$R_9$, each $T_1$ is independently selected from the group consisting of:
—CH=CH—,
—O—,
—S—,
—SO—,
—SO$_2$—,
—NR$_{10}$—,
—NR$_{10}$—CO—,
—CO—,
—O—CO—,
—CO—O—,
—CO—NR$_{10}$—,
—O—CO—NR$_{10}$—,
—NR$_{10}$—CO—O—,
—NR$_{10}$—CO—NR$_{10}$—,
—SO$_2$—NR$_{10}$—,
—NR$_{10}$—SO$_2$—, and
—NR$_{10}$—SO$_2$—NR$_{13}$, each $R_5$ is independently selected from the group consisting of:
—H,
—Ar$_1$,
—CO—Ar$_1$,
—SO$_2$—Ar$_1$,
—$R_9$,
—CO—$R_9$,
—CO—O—$R_9$,
—SO$_2$—$R_9$,

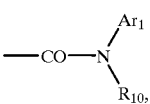

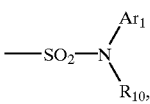

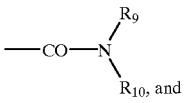

-continued

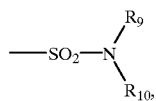

$R_6$ and $R_7$ taken together form a saturated 4–8 member carbocyclic ring or heterocyclic ring containing —O—, —S—, or —NH—, or $R_7$ is —H and $R_6$ is

—H

—$Ar_1$,

—$R_9$, or

—$(CH_2)_{1,2,3}$—$T_1R_9$;

each $R_9$ is a $C_{1-6}$ straight or branched alkyl group optionally singly or multiply substituted by —OH, —F, or =O and optionally substituted with one or two $Ar_1$ groups;

each Ric is independently selected from the group consisting of —H or a $C_{1-6}$ straight or branched alkyl group;

each $R_{13}$ is independently selected from the group consisting of —$Ar_2$ and —$R_4$, each $Ar_1$ is a cyclic group independently selected from the set consisting of an aryl group which contains 6, 10, 12, or 14 carbon atoms and between 1 and 3 rings, a cycloalkyl group which contains between 3 and 15 carbon atoms and between 1 and 3 rings, said cycloalkyl group being optionally benzofused, and a heterocycle group containing between 5 and 15 ring atoms and between 1 and 3 rings, said heterocycle group containing at least one heteroatom group selected from —O—, —S—, —SO—, —SO$_2$, =N—, and —NH—, said heterocycle group optionally containing one or more double bonds, said heterocycle group optionally comprising one or more aromatic rings, and said cyclic group optionally being singly or multiply substituted by =O, —OH, perfluoro $C_{1-3}$ alkyl, or —$Q_1$;

each $Ar_2$ is independently selected from the following group, in which any ring may optionally be substituted by —$Q_1$:

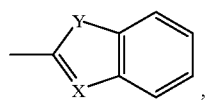 (hh)

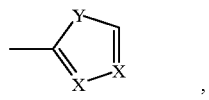 (ii)

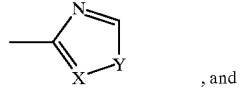 (jj) , and

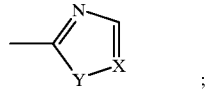 (kk) ;

$Ar_3$ is a cyclic group selected from the set consisting of a phenyl ring, a 5-membered heteroaromatic ring, and a 6-membered heteroaromatic ring, said heteroaromatic rings comprising 1–3 heteroatom groups selected from —O—, —S—, —SO—, —SO$_2$, =N—, and —NH—, said cyclic group optionally being singly or multiply substituted with —O, —OH, halogen, perfluoro $C_{1-3}$ alkyl, or —CO$_2$H;

each $Q_1$ is independently selected from the group consisting of

—$Ar_1$

—$R_9$,

—$T_1$—$R_9$, and

—$(CH_2)_{1,2,3}$—$T_1$—$R_9$, provided that when —$Ar_1$ is substituted with a $Q_1$ group which comprises one or more additional —$Ar_1$ groups, said additional —$Ar_1$ groups are not substituted with $Q_1$;

each X is independently selected from the group consisting of =N—, and =CH—;

each $X_2$ is independently selected from the group consisting of —O—, —CH$_2$—, —NH—, —S—, —SO—, and —SO$_2$—;

each $X_3$ is independently selected from the group consisting of —CH$_2$—, —S—, —SO—, and —SO$_2$—;

each $X_4$ is independently selected from the group consisting of —CH$_2$— and —NH—;

each $X_5$ is independently selected from the group consisting of

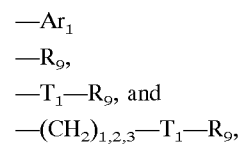

$X_6$ is CH or N, provided that when $X_6$ is N in the $R_1$ group labeled (o) and $X_5$ is CH and $X_2$ is CH$_2$ the ring of the $R_1$ group labeled (o) must be substituted by $Q_1$ or benzofused;

each Y is independently selected from the group consisting of —O— and —S—;

each Z is independently CO or SO$_2$, each a is independently 0 or 1, each c is independently 1 or 2, each d is independently 0, 1, or 2, each e is independently 0, 1, 2, or 3, either $R_{31}$ is —H or —$R_9$ and $R_{32}$ is

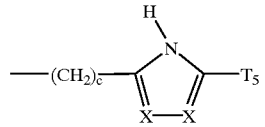 (pp)

or

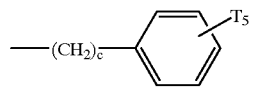 (qq)

or $R_{31}$ is —H and $R_{32}$ is

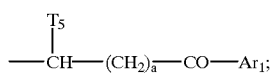   (5)

$R_{30}$ is selected from the group consisting of the following formulae, in which any ring may optionally be singly or multiply substituted by =O, —OH, —CO$_2$H, —Q$_1$, or halogen and in which any saturated ring may optionally be unsaturated at one or two bonds:

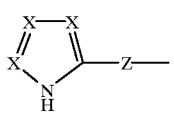   (rr)

or

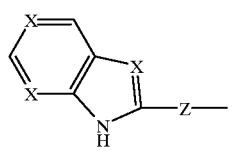   (ss)

or

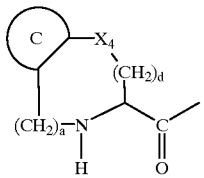   (tt)

or

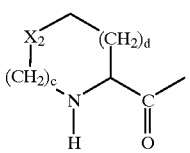   (uu)

or

   (50)

$A_1$ is a direct bond, an alpha-amino acid, or beta-alanine;
$A_2$ is a direct bond, an alpha-amino acid, or beta-alanine;
$T_5$ is —(CJ$_2$)$_m$—T,
$Y_4$ is —O—, —S—, —CH=CH—, or —NH—,
$X_7$ is —NH— or —CH$_2$—,
$R_{16}$ is selected from the group consisting of the following formulae, in which any ring may optionally be singly or multiply substituted at any carbon by Q$_1$, at any nitrogen by $R_5$, or at any atom by =O, —OH, —CO$_2$H, or halogen, and in which any saturated ring may optionally be unsaturated at one or two bonds:

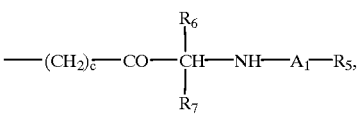   (ww)

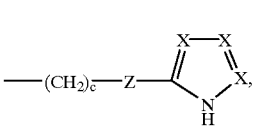   (xx)

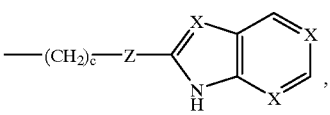   (yy)

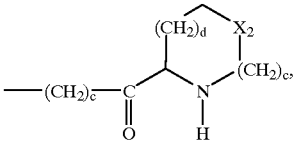   (zz)

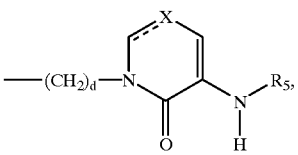   (aaa)

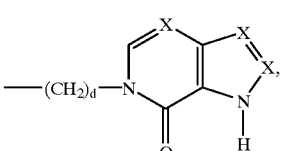   (bbb)

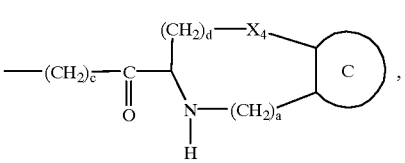   (ccc)

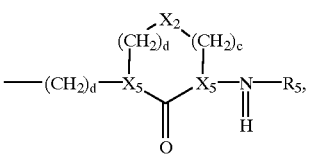   (ddd)

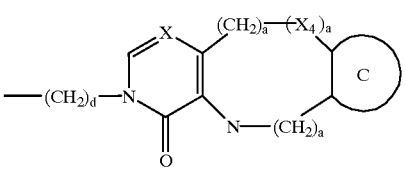   (eee)

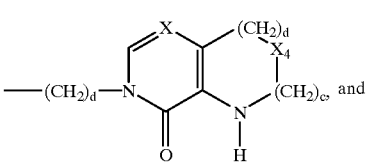   (fff)

and

-continued
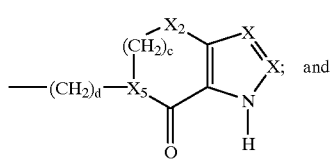 (ggg)
$Z_1$ is optionally C=O, S=O, or C=S.
Preferred forms of the $R_1$ group (a) are:
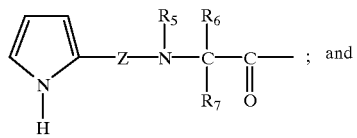 (a1)
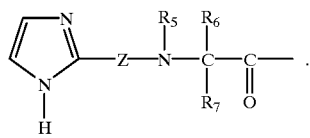 (a2)
Preferred forms of the $R_1$ group (b) are:
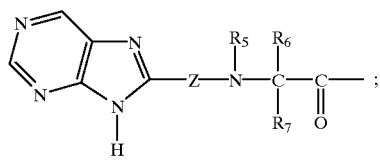 (b1)
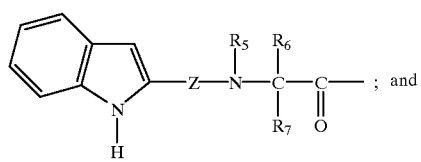 (b2)
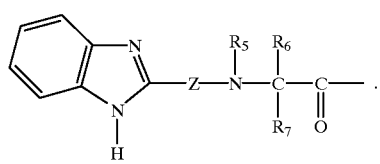 (b3)
Preferred forms of the $R_1$ group (c) are:
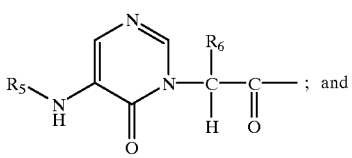 (c1)
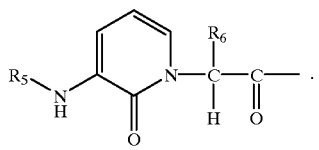 (c2)
Preferred forms of the $R_1$ group (d) are:
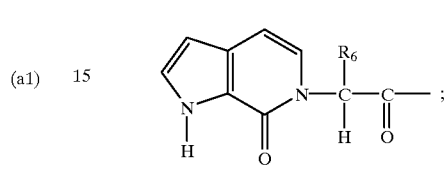 (d1)
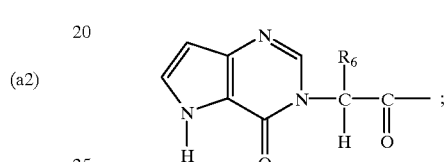 (d2)
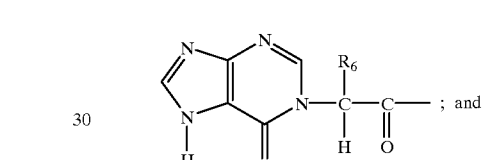 (d3)
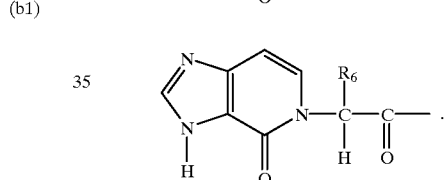 (d4)
Preferred forms of the $R_1$ group (e) are:
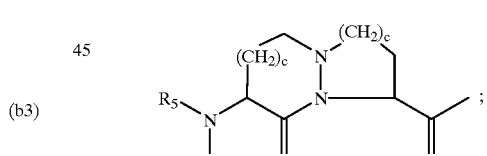 (e1)
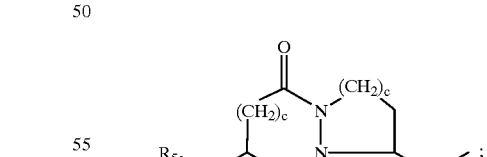 (e2)
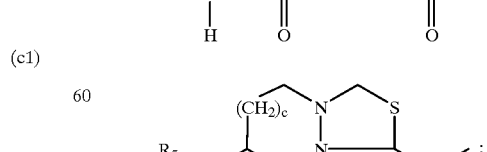 (e3)

(e4) 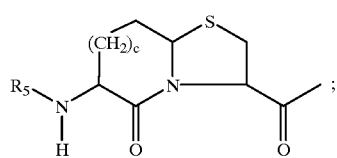
(e5) 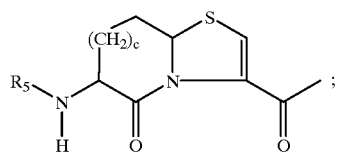
(e6) 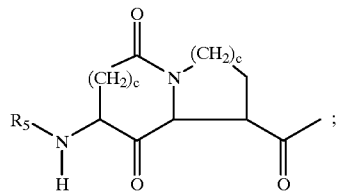
(e7) 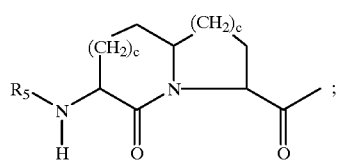
(e8) 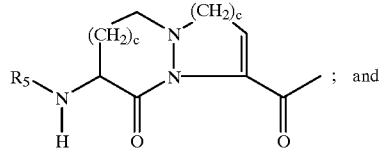
(e9) 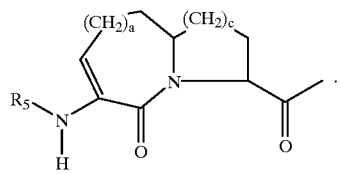
Preferred forms of the $R_1$ group (g) are:
(g1) 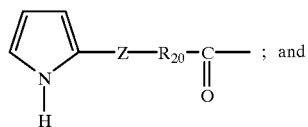
(g2) 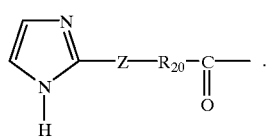
Preferred forms of the $R_1$ group (h) are:
(h1) 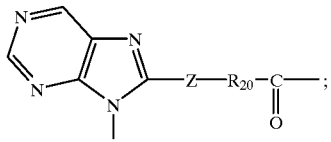
(h2) 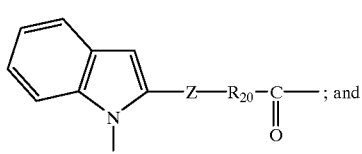
(h3) 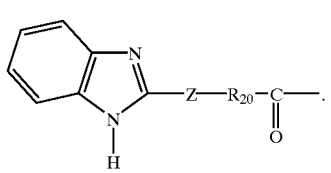
Preferred forms of the $R_1$ group (i) are:
(i1) 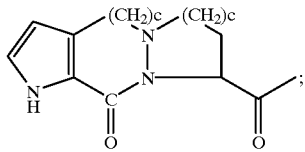
(i2) 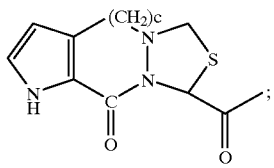
(i3) 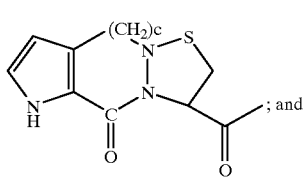
(i4) 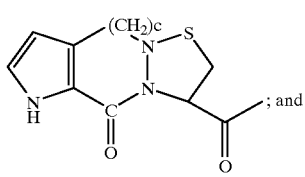

Preferred forms of the $R_1$ group (j) are:
(j1)
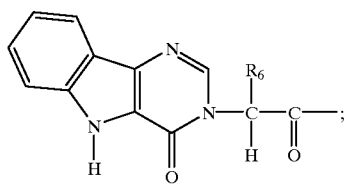
(j2)
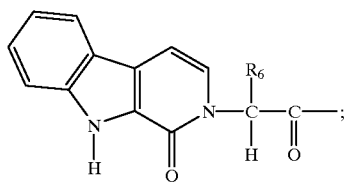
(j3)
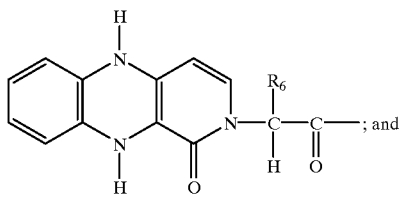
(j4)
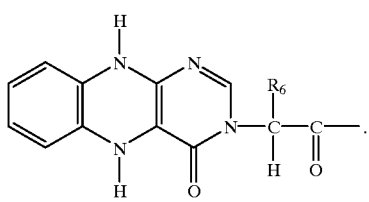
Preferred forms of the $R_1$ group (k) are:
(k1)
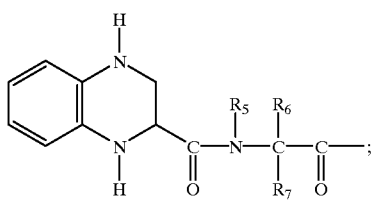
(k2)
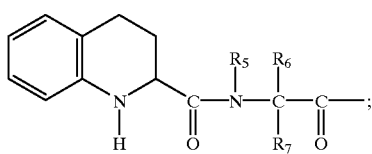
(k3)
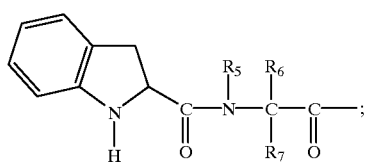
(k4)
(k5)
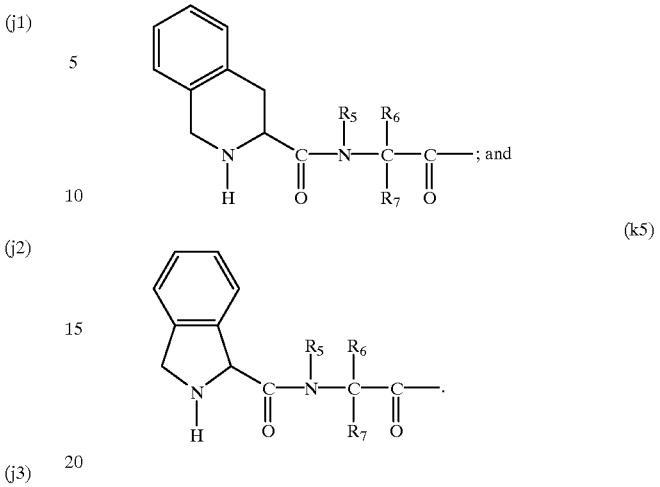
Preferred forms of the $R_1$ group (l) are:
(l1)
(l2)
(l3)
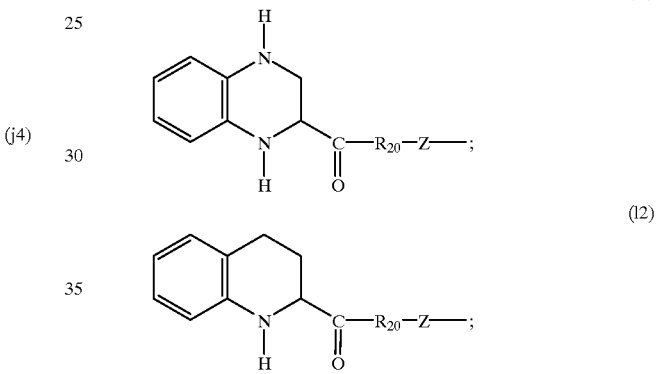
(l4)
(l5)
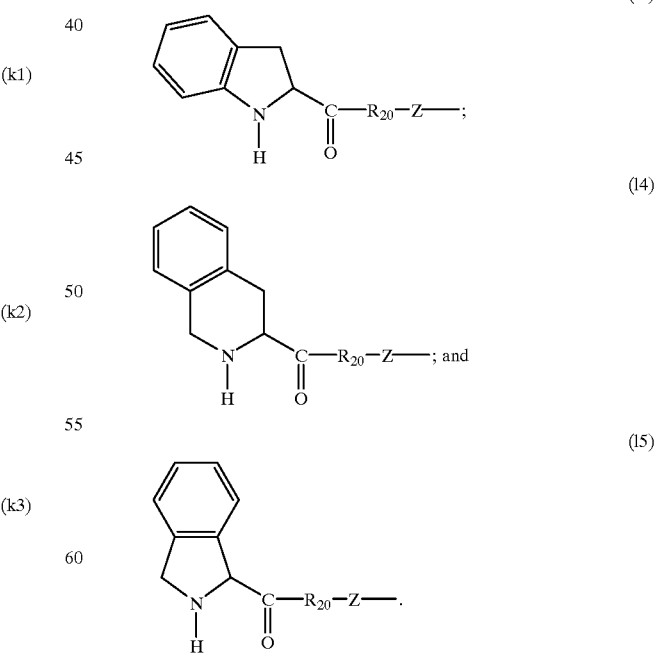

Preferred forms of the $R_1$ group (m) are:
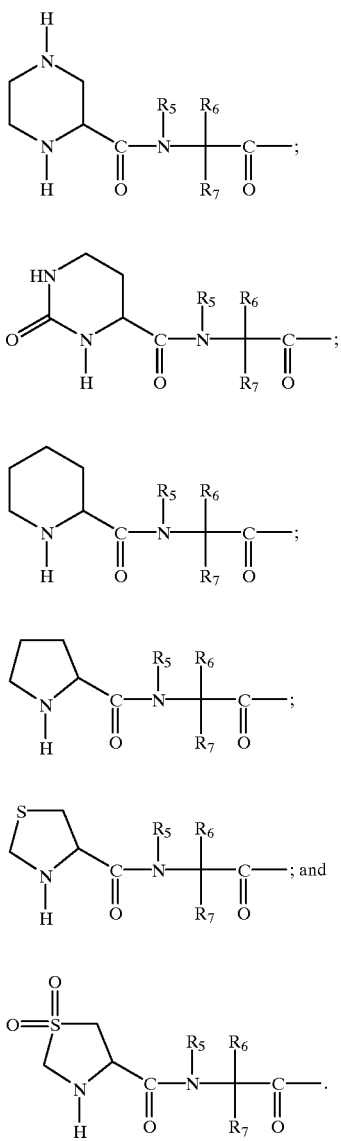
Preferred forms of the $R_1$ group (n) are:
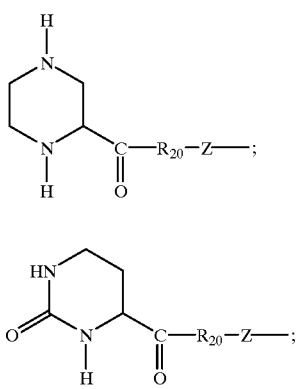
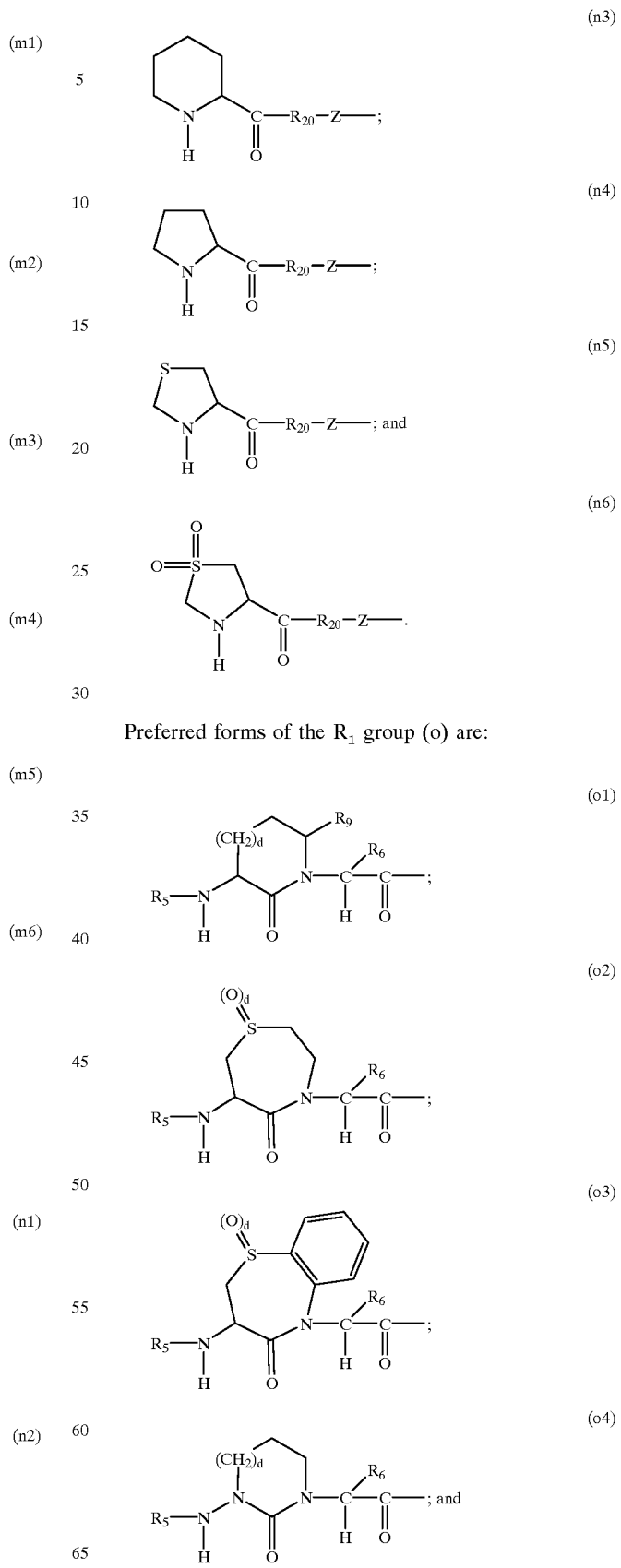
Preferred forms of the $R_1$ group (o) are:

(o5)
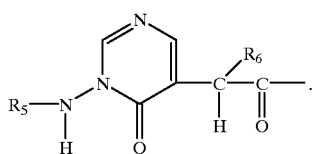
Preferred forms of the R₁ group (p) are:
(p1)
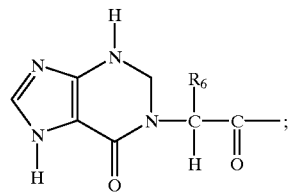
(p2)
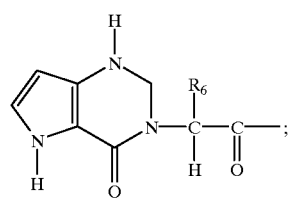
(p3)
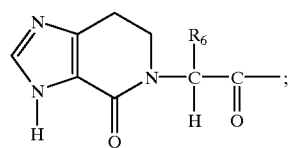
(p4)
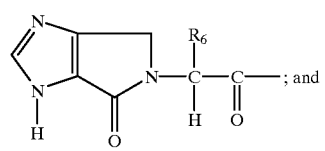
(p5)
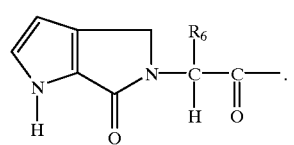
Preferred forms of the R₁ group (q) are:
(q1)
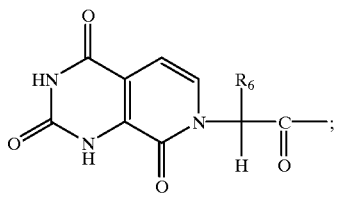
(q2)
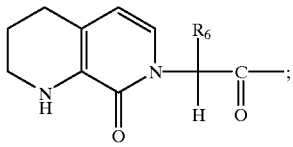
(q3)
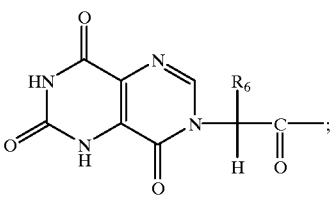
(q4)
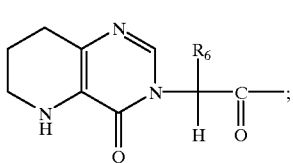
(q5)
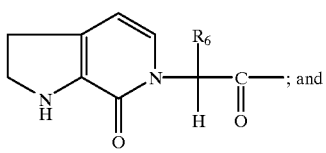
(q6)
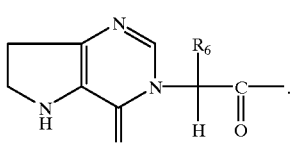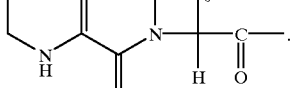
Preferred forms of the R₁ group (r) are:
(r1)
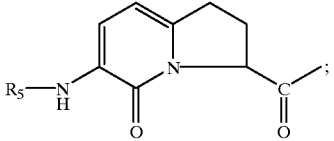
(r2)
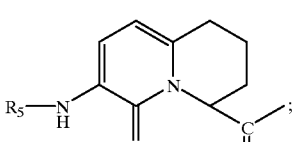
(r3)
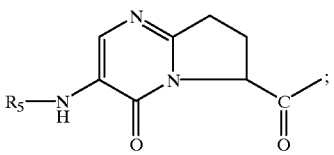

-continued
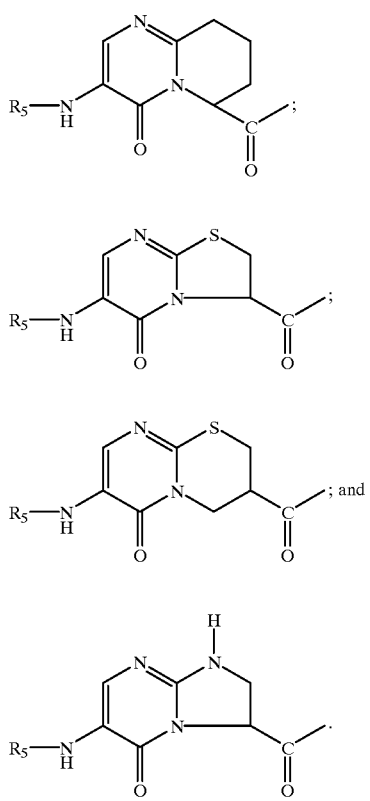
(r4)
(r5)
(r6)
(r7)
Preferred forms of the $R_1$ group (s) are:
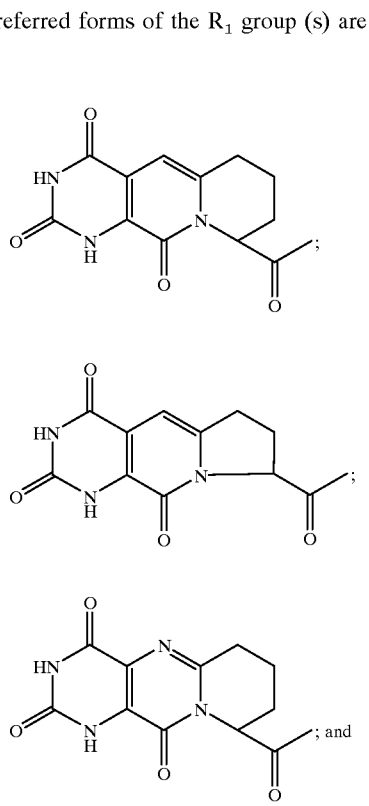
(s1)
(s2)
(s3)
-continued
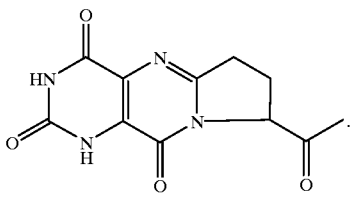
(s4)
Preferred forms of the $R_1$ group (t) are:
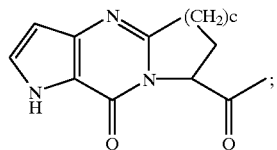
(t1)
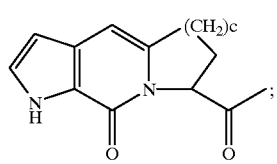
(t2)
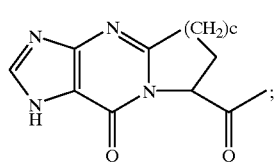
(t3)
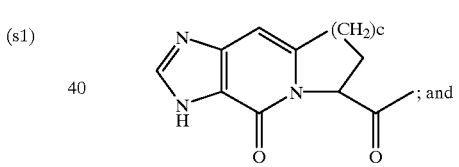
(t4)
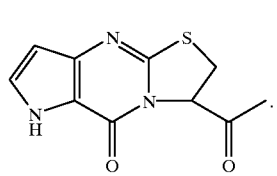
(t5)
Preferred forms of the $R_1$ group (v) are:
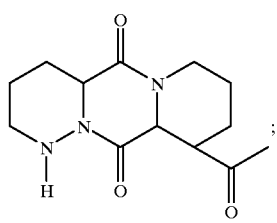
(v1)

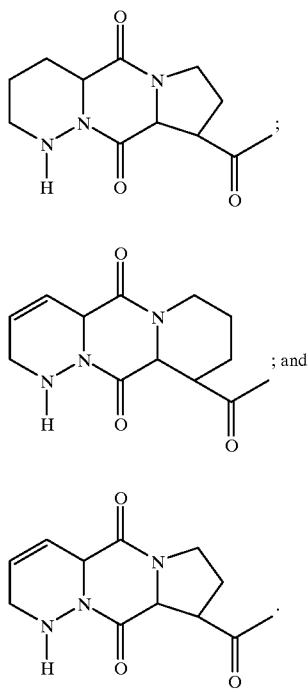

(v2)

(v3)

(v4)

The most preferred compounds of this invention are those which employ formula α, wherein:

$X_1$ is CH;

g is O;

J is —H;

m is 0 or 1 and T is —$Ar_3$, —CO—$CO_2H$, —$CO_2H$ or any bioisosteric replacement for —$CO_2H$, or m is 1 or 2 and T is —OH, —$CF_3$, or —$CO_2H$;

most preferably m is 1 and T is —$CO_2H$;

$R_1$ is

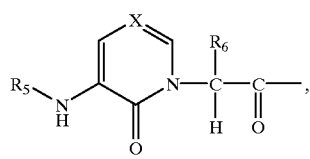 (c)

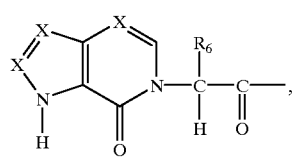 (d)

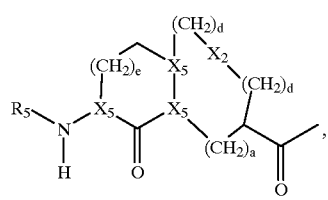 (e)

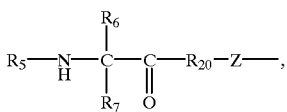 (f)

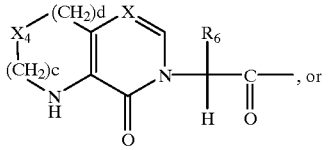 (q)

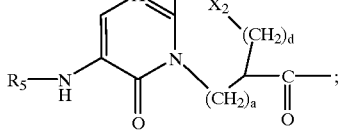 (r)

$R_{20}$ is

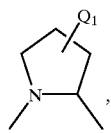 (aa1)

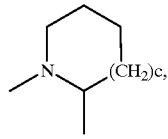 (aa2)

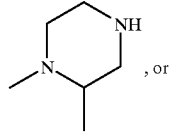 (aa3)

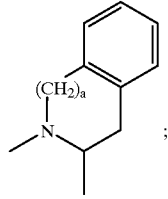 (dd)

wherein ring C is benzo;

$R_3$ is

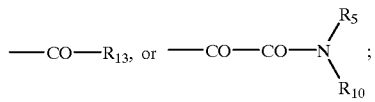

most preferably $R_3$ is any one of 1), 2) or 3) as follows:
1) —CO—$Ar_2$, 2) —CO—RG where Rg is $C_{3-6}$ alkyl substituted with two $Ar_1$ groups or one $Ar_1$ group itself substituted with an $Ar_1$ group, —$C_{1-2}$—$Ar_1$, —Cl, —$CH_3$, or —$CF_3$, or 3) —$(CH_2)_{1,2}$—$T_1$—$R_9$ where $T_1$ is —O— or —S— and $R_9$ is $C_{12}$ alkyl substituted with two $Ar_1$ groups or one $Ar_1$ group itself substituted with an $Ar_1$ group, $C_{1-2}$—$Ar_1$, —Cl, —$CH_3$, or —$CF_3$;

R$_4$ is —H or —R$_9$;
T$_1$ is
—S—,
—CO—,
—O—CO—, or
—SO$_2$—;
when R$_1$ is (a), (b), (k), or (m), R$_5$ is preferably —Ar$_1$ or C$_{1-4}$—Ar$_1$;
when R$_1$ is (c), (e), (f), (o), or (r), R$_5$ is preferably —SO$_2$—Ar$_1$, —SO$_2$—R$_9$, or —CO—C$_{1-4}$—Ar$_1$;
R7 is —H and R$_6$ is C$_{1-4}$—Ar$_1$;
R$_{10}$ is —H or a C$_{1-3}$ straight or branched alkyl group;
R$_{13}$ is —Ar$_2$;
Ar$_1$ is phenyl, naphthyl, pyridyl, benzothiazolyl, thienyl, benzothienyl, benzoxazolyl, 2-indanyl, or indolyl;
Ar$_2$ is preferably substituted with —Ar$_1$, or —C$_{1-4}$—Ar$_1$;
Ar$_3$ is phenyl, thiophene, thiazole, pyridine, or oxazole; and
Q$_1$ is —R$_9$ or —(CH$_2$)$_{1,2}$—T$_1$—(CH$_2$)$_{1-3}$—Ar$_1$ where T$_1$ is —O— or —S—.

For preferred compounds which employ formula β, R$_{31}$ is R$_9$ and R$_{32}$ is (pp), wherein c is 1 or 2, X is C, J is H, m is 1 or 2, and T is —CO$_2$H. In addition, the preferred R$_{30}$ groups are (rr) and (ss).

Preferred forms of (rr) are:

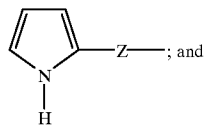

(rr1)

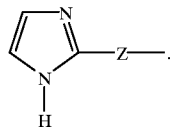

(rr2)

Preferred forms of (ss) are:

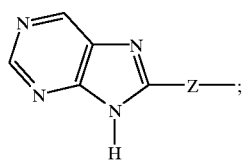

(ss1)

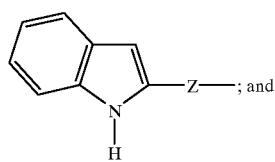

(ss2)

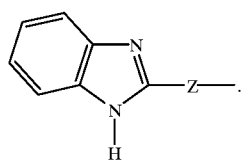

(ss3)

For preferred compounds which employ formula (vv), Y$_4$ is —O— or —S—, X$_7$ is —NH—, J is H, m and T are 2 and —CO$_2$H or 1 and —CO—CO$_2$H, and R$_{16}$ is (yy), (aaa), or (fff).

For preferred compounds which employ formula (hhh), Z$_1$ is carbonyl, J is H, f is 1 or 2, T is —CO$_2$H, and R$_{16}$ is (ww), (xx), (yy), (aaa), or (fff).

In the preferred form of (ww), c is 2, R$_6$ is isopropyl, R$_7$ is H, A$_1$ is any natural amino acid, and R$_5$ is acetyl or benzyloxycarbonyl.

Preferred forms of (xx) are:

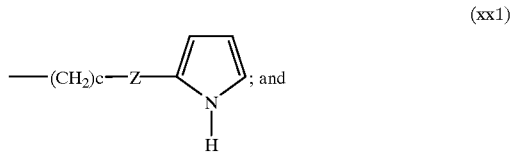

(xx1)

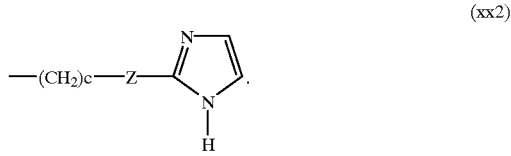

(xx2)

Preferred forms of (yy) are:

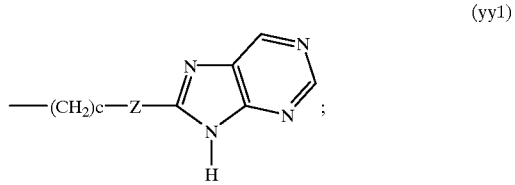

(yy1)

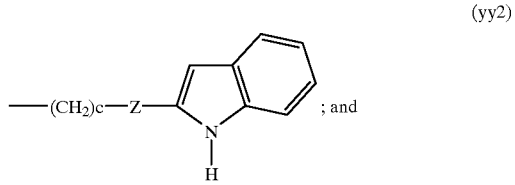

(yy2)

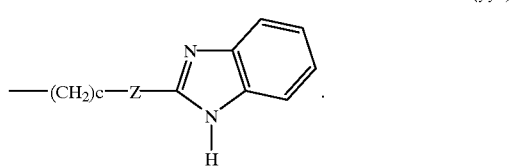

(yy3)

In the prefered forms of (aaa), d is 1 and R$_5$ is —H, —CO—O—R$_9$, —SO$_2$—R$_9$, or —SO$_2$—Ar$_1$.

Preferred forms of (fff) are:

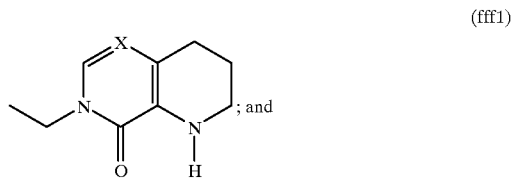

(fff1)

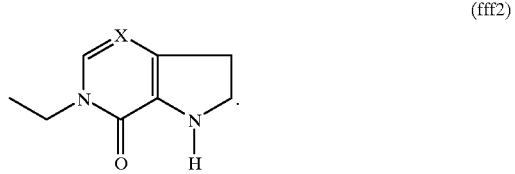

(fff2)

The compounds of this invention having a molecular weight of less than or equal to about 700 Daltons, and more preferably between about 400 and 600 Daltons, are prefered. These prefered compounds may be readily absorbed by the bloodstream of patients upon oral administration. This oral availability makes such compounds excellent agents for orally-administered treatment and prevention regimens against IL-1 mediated diseases.

The ICE inhibitors of this invention may be synthesized using conventional techniques. Advantageously, these compounds are conveniently synthesized from readily available starting materials.

The compounds of this invention are among the most readily synthesized ICE inhibitors known. Previously described ICE inhibitors often contain four or more chiral centers and numerous peptide linkages. The relative ease with which the compounds of this invention can be synthesized represents an enormous advantage in the large scale production of these compounds.

It should be understood that the compounds of this invention may exist in various equilibrium forms, depending on conditions including choice of solvent, pH, and others known to the practitioner skilled in the art. All such forms of these compounds are expressly included in the present invention. In particular, many of the compounds of this invention, especially those which contain aldehyde or ketone groups in $R_3$ and carboxylic acid groups in T, may take hemi-ketal (or hemi-acetal) or hydrated forms, as depicted below:

biological penetration into a given biological system (e.g., blood, lymphatic system, central nervous system), increase oral availability, increase solubility to allow administration by injection, alter metabolism and alter rate of excretion. In addition, the compounds may be altered to pro-drug form such that the desired compound is created in the body of the patient as the result of the action of metabolic or other biochemical processes on the pro-drug. Such pro-drug forms may include ketal or acetal forms of compounds which contain ketone or aldehyde groups, especially where they occur in the $R_3$ group of the compounds of this invention.

The compounds of this invention are excellent ligands for ICE. Accordingly, these compounds are capable of targeting and inhibiting events in IL-1 mediated diseases, such as the conversion of precursor IL-1β to mature IL-1β and, thus, the ultimate activity of that protein in inflammatory diseases, autoimmune diseases and neurodegenerative diseases. For example, the compounds of this invention inhibit the conversion of precursor IL-1β to mature IL-1β by inhibiting ICE. Because ICE is essential for the production of mature IL-1, inhibition of that enzyme effectively blocks initiation of IL-1 mediated physiological effects and symptoms, such as inflammation, by inhibiting the production of mature IL-1. Thus, by inhibiting IL-1β precursor activity, the compounds of this invention effectively function as IL-1 inhibitors.

The compounds of this invention may be employed in a conventional manner for the treatment of diseases which are (EQ1)

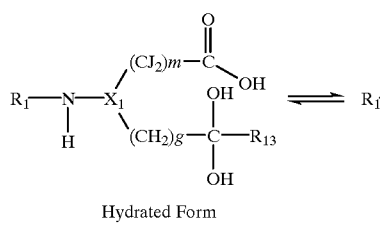 ⇌ 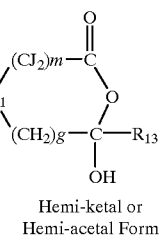 ⇌

Hydrated Form          Hemi-ketal or Hemi-acetal Form

Depending on the choice of solvent and other conditions known to the practitioner skilled in the art, compounds of this invention may also take acyloxy ketal, acyloxy acetal, ketal or acetal form:

mediated by IL-1. Such methods of treatment, their dosage levels and requirements may be selected by those of ordinary skill in the art from available methods and techniques. For example, a compound of this invention may be com- (EQ2)

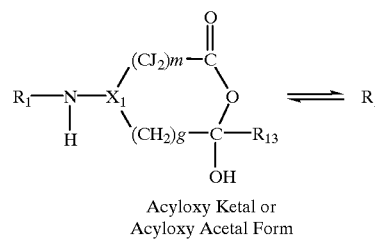 ⇌ ⇌ 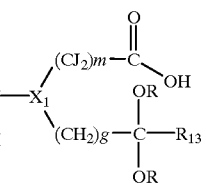

Acyloxy Ketal or Acyloxy Acetal Form          Ketal or Acetal Form

In addition, it should be understood that the equilibrium forms of the compounds of this invention may include tautomeric forms. All such forms of these compounds are expressly included in the present invention.

It should be understood that the compounds of this invention may be modified by appropriate functionalities to enhance selective biological properties. Such modifications are known in the art and include those which increase bined with a pharmaceutically acceptable adjuvant for administration to a patient suffering from an IL-1 mediated disease in a pharmaceutically acceptable manner and in an amount effective to lessen the severity of that disease.

Alternatively, the compounds of this invention may be used in compositions and methods for treating or protecting individuals against IL-1 mediated diseases over extended periods of time. The compounds may be employed in such compositions either alone or together with other compounds of this invention in a manner consistent with the conventional utilization of ICE inhibitors in pharmaceutical compositions. For example, a compound of this invention may be combined with pharmaceutically acceptable adjuvants conventionally employed in vaccines and administered in prophylactically effective amounts to protect individuals over an extended period time against IL-1 mediated diseases.

The compounds of this invention may also be co-administered with other ICE inhibitors to increase the effect of therapy or prophylaxis against various IL-1-mediated diseases.

In addition, the compounds of this invention may be used in combination either conventional anti-inflammatory agents or with matrix metalloprotease inhibitors, lipoxygenase inhibitors and antagonists of cytokines other than IL-1β.

The compounds of this invention can also be administered in combination with immunomodulators (e.g., bropirimine, anti-human alpha interferon antibody, IL-2, GM-CSF, methionine enkephalin, interferon alpha, diethyldithiocarbamate, tumor necrosis factor, naltrexone and rEPO) or with prostaglandins, to prevent or combat IL-1-mediated disease symptoms such as inflammation.

When the compounds of this invention are administered in combination therapies with other agents, they may be administered sequentially or concurrently to the patient. Alternatively, pharmaceutical or prophylactic compositions according to this invention may be comprised of a combination of an ICE inhibitor of this invention and another therapeutic or prophylactic agent.

Pharmaceutical compositions of this invention comprise any of the compounds of the present invention, and pharmaceutically acceptable salts thereof, with any pharmaceutically acceptable carrier, adjuvant or vehicle. Pharmaceutically acceptable carriers, adjuvants and vehicles that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The pharmaceutical compositions of this invention may be administered orally, parenterally, by inhalation spray, topically, rectally, nasally, buccally, vaginally or via an implanted reservoir. We prefer oral administration. The pharmaceutical compositions of this invention may contain any conventional non-toxic pharmaceutically-acceptable carriers, adjuvants or vehicles. The term parenteral as used herein includes subcutaneous, intracutaneous, intravenous, intramuscular, intra-articular, intrasynovial, intrasternal, intrathecal, intralesional and intracranial injection or infusion techniques.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant such as Ph. Helv or a similar alcohol.

The pharmaceutical compositions of this invention may be orally administered in any orally acceptable dosage form including, but not limited to, capsules, tablets, and aqueous suspensions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are administered orally, the active ingredient is combined with emulsifying and suspending agents. If desired, certain sweetening and/or flavoring and/or coloring agents may be added.

The pharmaceutical compositions of this invention may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

Topical administration of the pharmaceutical compositions of this invention is especially useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of this invention may also be topically applied to the lower intestinal tract by rectal suppository formulation or in a suitable enema formulation. Topically-transdermal patches are also included in this invention.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

The IL-1 mediated diseases which may be treated or prevented by the compounds of this invention include, but are not limited to, inflammatory diseases, autoimmune diseases and neurodegenerative diseases.

Inflammatory diseases which may be treated or prevented include, for example, septic shock, septicemia, and adult respiratory distress syndrome. Target autoimmune diseases include, for example, rheumatoid, arthritis, systemic lupus erythematosus, scleroderma, chronic thyroiditis, Graves' disease, autoimmune gastritis, insulin-dependent diabetes mellitus, autoimmune hemolytic anemia, autoimmune neutropenia, thrombocytopenia, chronic active hepatitis, myasthenia gravis and multiple sclerosis. And target neurodegenerative diseases include, for example, amyotrophic lateral sclerosis, Alzheimer's disease, Parkinson's disease, and primary lateral sclerosis. The ICE inhibitors of this invention may also be used to promote wound healing. And the ICE inhibitors of this invention may be used to treat infectious diseases.

Although this invention focuses on the use of the compounds disclosed herein for preventing and treating IL-1-mediated diseases, the compounds of this invention can also be used as inhibitory agents for other cysteine proteases.

The compounds of this invention are also useful as commercial reagents which effectively bind to ICE or other cysteine proteases. As commercial reagents, the compounds of this invention, and their derivatives, may be used to block proteolysis of a target peptide or may be derivatized to bind to a stable resin as a tethered substrate for affinity chromatography applications. These and other uses which characterize commercial cysteine protease inhibitors will be evident to those of ordinary skill in the art.

In order that this invention be more fully understood, the following examples are set forth. These examples are for the purpose of illustration only and are not to be construed as limiting the scope of the invention in any way.

EXAMPLE 1

The following example demonstrates a process of drug design which embodies the present invention:

Step 1) Pick 2 hydrogen bonding moieties of ICE, here, the backbone C=O and N—H of Arg-341.

Step 2) Pick a scaffold, here, a pyridone derivative, and confirm that the hydrogen bonding moieties of the scaffold are capable of forming satisfactory hydrogen bonds with the hydrogen bonding moieties selected in step 1. This confirmation is performed by using molecular mechanics techniques to minimize the scaffold fragment in the context of the active site of ICE.

(Z1)

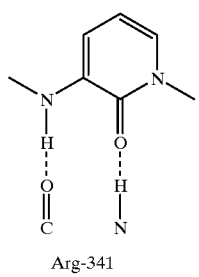

Arg-341

Step 3) Pick a hydrophobic pocket, here, S2, as next target and a hydrophobic moiety, here, benzene. Minimize the benzene group within the S2 pocket to assure that substantial hydrophobic overlap is obtained.

(Z2)

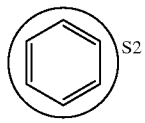

Step 4) Pick another hydrophobic pocket, here, S4, as the next target and a hydrophobic moiety, here, benzene. Minimize the benzene group within the S4 pocket to ensure that substantial hydrophobic overlap is obtained.

(Z3)

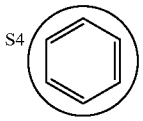

Step 5) Fill the S1 polar pocket with an electronegative moiety, here, a carboxylate sidechain provided by aspartic acid in which the C-terminus has been reduced to an aldehyde. Minimize to ensure that the carboxylate sidechain retains a favorable electrostatic interaction with the S1 polar pocket.

(Z4)

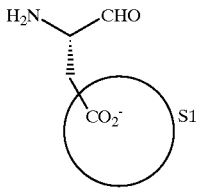

Step 6) Link the scaffold with the moieties from steps 3, 4, and 5, preferably using the minimum number of bonds consistent with a chemically reasonable structure. Minimize the entire composite molecule in the active site of ICE.

(Z5)

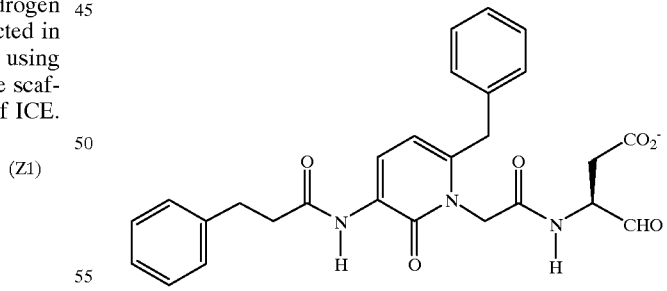

Step 7) Evaluate the energy of the molecule when it has the conformation necessary for binding to ICE. Then minimize and reevaluate the energy—this is the free conformation energy. The strain energy for binding of the potential inhibitor to ICE is the difference between the free conformation energy and the bound conformation energy. The strain energy should be less than about 10 kcal/mol. In this case the bound conformation energy is −1.6 kcal/mol and the free conformation energy is −11.7 kcal/mol, for a strain energy of 10.1 kcal/mol.

Step 8) The inhibitor designed using the above steps has been made and has been show to have a $K_i$ of 150 nM.

EXAMPLE 2

We obtained inhibition constants and $IC_{50}$ values for several compounds of this invention using the three methods described below:

1. Enzyme assay with UV-visible substrate

This assay is run using an Succinyl-Tyr-Val-Ala-Asp-pNitroanilide substrate. Synthesis of analogous substrates is described by L. A. Reiter (Int. J. Peptide Protein Res. 43, 87–96 (1994)). The assay mixture contains:

| | |
|---|---|
| 65 μl | buffer (10 mM Tris, 1 mM DTT, 0.1% CHAPS @ pH 8.1) |
| 10 μl | ICE (50 nM final concentration to give a rate of ~1 mOD/min) |
| 5 μl | DMSO/Inhibitor mixture |
| 20 μl | 400 μM Substrate (80 μM final concentration) |
| 100 μl | total reaction volume |

The visible ICE assay is run in a 96-well microtiter plate. Buffer, ICE and DMSO (if inhibitor is present) are added to the wells in the order listed. The components are left to incubate at room temperature for 15 minutes starting at the time that all components are present in all wells. The microtiter plate reader is set to incubate at 37° C. After the 15 minute incubation, substrate is added directly to the wells and the reaction is monitored by following the release of the chromophore (pNA) at 405–603 nm at 37° C. for 20 minutes. A linear fit of the data is performed and the rate is calculated in mOD/min. DMSO is only present during experiments involving inhibitors, buffer is used to make up the volume to 100 μl in the other experiments.

2. Enzyme Assay with Fluorescent Substrate

This assay is run essentially according to Thornberry et al. (Nature 356: 768–774 (1992)), using substrate 17 referenced in that article. The substrate is: Acetyl-Tyr-Val-Ala-Asp-amino-4-methylcoumarin (AMC). The following components are mixed:

| | |
|---|---|
| 65 μl | buffer (10 mM Tris, 1 mM DTT, 0.1% CHAPS @ pH 8.1) |
| 10 μl | ICE (2–10 nM final concentration) |
| 5 μl | DMSO/inhibitor solution |
| 20 μl | 150 μM Substrate (30 μM final) |
| 100 μl | total reaction volume |

The assay is run in a 96 well microtiter plate. Buffer and ICE are added to the wells. The components are left to incubate at 37° C. for 15 minutes in a temperature-controlled wellplate. After the 15 minute incubation, the reaction is started by adding substrate directly to the wells and the reaction is monitored @37C for 30 minutes by following the release of the AMC fluorophore using an excitation wavelength for 380 nm and an emission wavelength of 460 nm. A linear fit of the data for each well is performed and a rate is determined in fluorescence units per second.

For determination of enzyme inhibition constants ($K_i$) or the mode of inhibition (competitive, uncompetitive or noncompetitive), the rate data determined in the enzyme assays at varying inhibitor concentrations are computer-fit to standard enzyme kinetic equations (see I. H. Segel, *Enzyme Kinetics*, Wiley-Interscience, 1975).

3. Cell assay

IL-1β Assay with a Mixed Population of Human Peripheral Blood Mononuclear Cells (PBMC) or Enriched Adherent Mononuclear Cells Processing of pre-IL-1β by ICE can be measured in cell culture using a variety of cell sources. Human PBMC obtained from healthy donors provides a mixed population of lymphocyte subtypes and mononuclear cells that produce a spectrum of interleukins and cytokines in response to many classes of physiological stimulators. Adherent mononuclear cells from PBMC provides an enriched source of normal monocytes for selective studies of cytokine production by activated cells.

Experimental Procedure:

An initial dilution series of test compound in DMSO or ethanol is prepared, with a subsequent dilution into RPMI-10% FBS media (containing 2 mM L-glutamine, 10 mM HEPES, 50 U and 50 ug/ml pen/strep) respectively to yield drugs at 4× the final test concentration containing 0.4% DMSO or 0.4% ethanol. The final concentration of DMSO is 0.1% for all drug dilutions. A concentration titration which brackets the apparent $K_i$ for a test compound determined in an ICE inhibition assay is generally used for the primary compound screen.

We generally test 5–6 compound dilutions and have performed the cellular component of the assay in duplicate, with duplicate ELISA determinations on each cell culture supernatant.

PBMC Isolation and IL-1 Assay:

Buffy coat cells isolated from one pint human blood (yielding 40–45 ml final volume plasma plus cells) are diluted with media to 80 ml and LeukoPREP separation tubes (Becton Dickinson) are each overlaid with 10 ml of cell suspension. After 15 min centrifugation at 1500–1800× g, the plasma/media layer is aspirated and then the mononuclear cell layer is collected with a Pasteur pipette and transferred to a 15 ml conical centrifuge tube (Corning). Media is added to bring the volume to 15 ml, gently mix the cells by inversion and centrifuge at 300× g for 15 min. Resuspend the PBMC pellet in a small volume of media, count cells and adjust to $6 \times 10^6$ cells/ml.

For the cellular assay, add 1.0 ml of the cell suspension to each well of a 24-well flat bottom tissue culture plate (Corning), 0.5 ml test compound dilution and 0.5 ml LPS solution (Sigma #L-3012; 20 ng/ml solution prepared in complete RPMI media; final LPS concentration 5 ng/ml). The 0.5 ml additions of test compound and LPS are usually sufficient to mix the contents of the wells. Three control mixtures are run per experiment, with either LPS alone, solvent vehicle control, and/or additional media to adjust the final culture volume to 2.0 ml. The cell cultures are incubated for 16–18 hr at 37° C. in the presence of 5% $CO_2$.

At the end of the incubation period, cells are harvested and transferred to 15 ml conical centrifuge tubes. After centrifugation for 10 min at 200× g, supernatants are harvested and transferred to 1.5 ml Eppendorf tubes. It may be noted that the cell pellet may be utilized for a biochemical evaluation of pre-IL-1β and/or mature IL-1β content in cytosol extracts by western blotting or ELISA with pre-IL-1β specific antisera.

Isolation of Adherent Mononuclear cells:

PBMC are isolated and prepared as described above. Media (1.0 ml) is first added to wells followed by 0.5 ml of the PBMC suspension. After a one hour incubation, plates are gently shaken and nonadherent cells aspirated from each well. Wells are then gently washed three times with 1.0 ml of media and final resuspended in 1.0 ml media. The enrichment for adherent cells generally yields $2.5$–$3.0 \times 10^5$ cells per well. The addition of test compounds, LPS, cell incubation conditions and processing of supernatants proceeds as described above.

ELISA:

We have used Quantikine kits (R&D Systems) for measurement of mature IL-1β. Assays are performed according to the manufacturer's directions. Mature IL-1β levels of about 1–3 ng/ml in both PBMC and adherent mononuclear cell positive controls are observed. ELISA assays are performed on 1:5, 1:10 and 1:20 dilutions of supernatants from LPS-positive controls to select the optimal dilution for supernatants in the test panel.

The inhibitory potency of the compounds can be represented by an $IC_{50}$ value, which is the concentration of inhibitor at which 50% of mature IL-1β is detected in the supernatant as compared to the positive controls.

The following $K_i$ and $IC_{50}$ values were determined for compounds A through N using the indicated assays. Structures for compounds A through N follow this table.

| Compound | $K_i$ ($\mu$M), by indicated assay: | | |
|---|---|---|---|
| | UV-visible $K_i$ ($\mu$M) | Fluorescence $K_i$ ($\mu$M) | Cell $IC_{50}$ ($\mu$M) |
| A | 5.5 | | 25.0 |
| B | 8.6 | | 20.0 |
| C | 10 | | >30 |
| D | 4.7 | | |
| E | 3.2 | | |
| F | 0.15 | | 2–4 |
| G | 4.8 | | |
| H | 0.023 | 0.0047 | 6–11 |
| I | 0.0072 | 0.0052 | 2.6 |
| J | 0.0012 | 0.0039 | 5–7 |
| K | 0.010 | 0.002 | 2–11 |
| L | 0.014 | | |
| M | 0.15 | | |
| N | 0.95 | | |

Structures of compounds A through N:

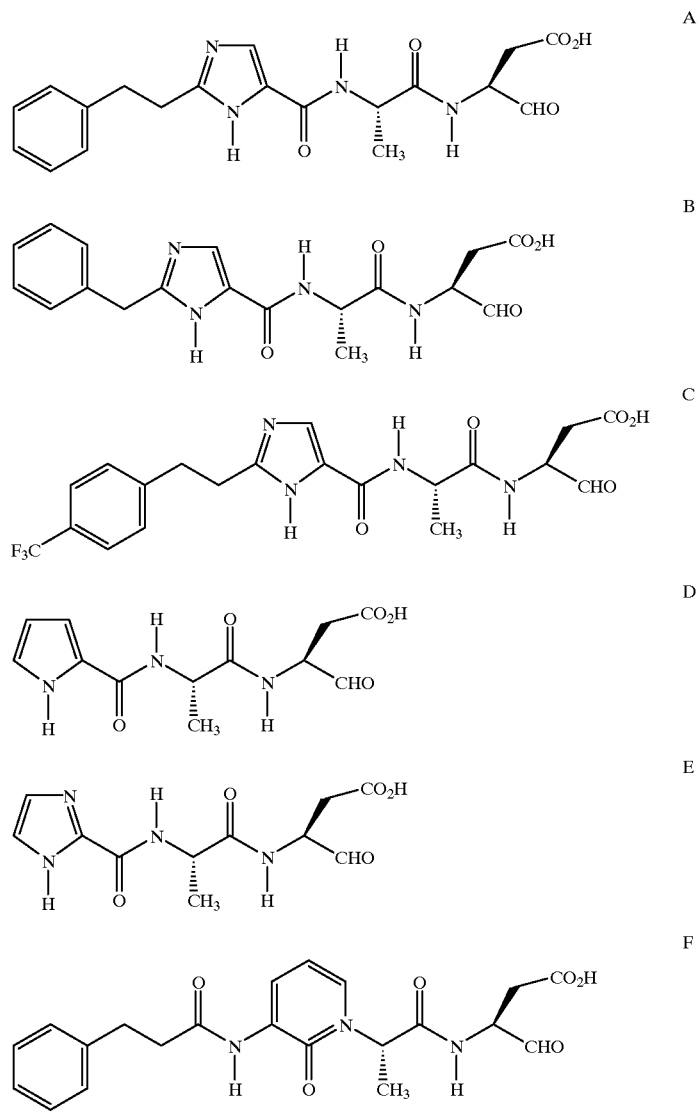

G
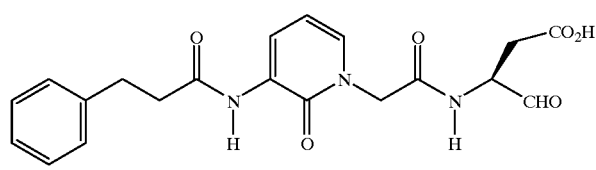
H
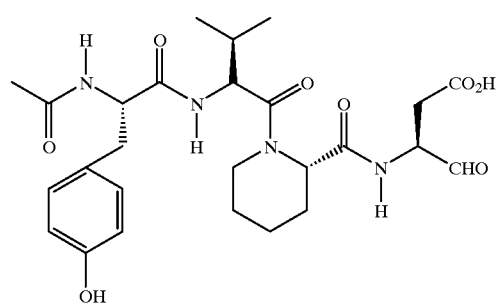
I
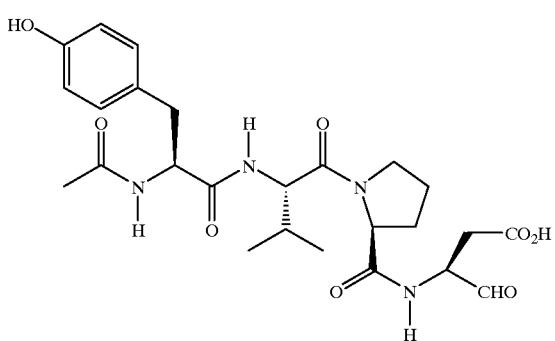
J
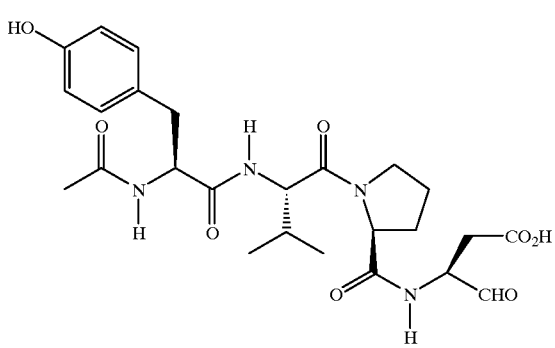
K
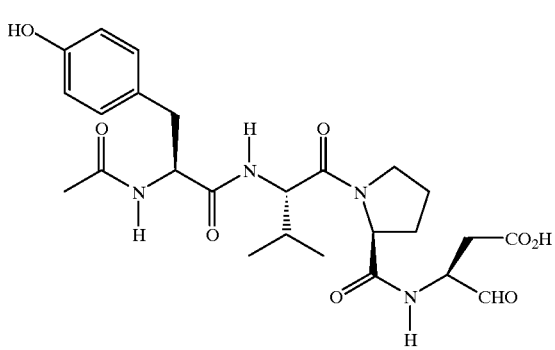

L

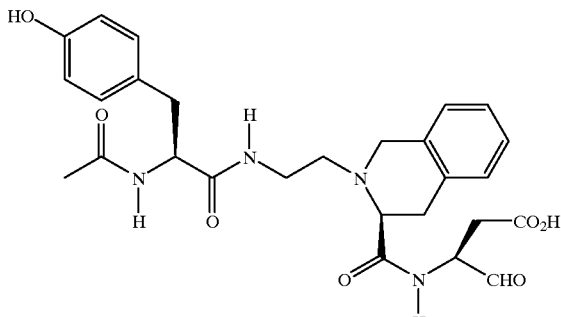

M

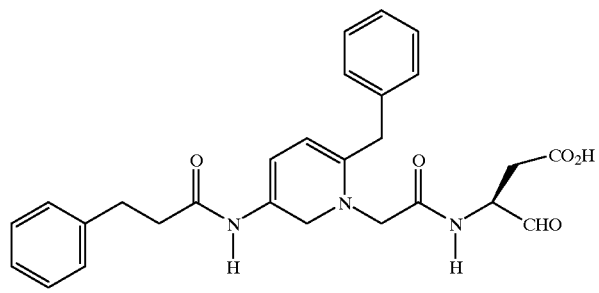

N

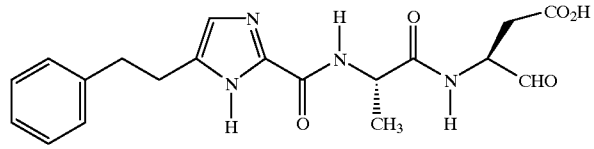

EXAMPLE 3

Compounds of Example 2 were synthesized as follows:
H. N-(N-Acetyl-tyrosinyl-valinyl-pipecolyl)-3-amino-4-oxobutanoic acid.

Step A. N-(N-tert-Butoxycarbonylpipecolyl)-4-amino-5-benzyloxy-2-oxotetrahydrofuran.

Reaction of N-tert-butoxycarbonylpipecolic acid (460 mg, 2.0 mmol) and N-allyloxycarbonyl-4-amino-5-benzyloxy-2-oxotetrahydrofuran (530 mg, 1.82 mmol) was carried out by a method analogous to that reported by Chapman (Bioorg. & Med. Chem. Lett. 1992, 2, 613–618.) to give 654 mg of the title compound.

1H NMR (500 MHz, $CDCl_3$ (existing as rotomers)) 7.35 (m, 5H), 6.88 (br. s, 1H), 4.9–4.45(m, 4H), 3.95 (br. m, 2H), 3.06 (m, 1H), 2.9 (m, 1H), 2.7 (br. m, 1H), 2.45 (m, 1H), 2.2 (m, 1H), 1.7–1.5 (m, 3H), 1.45 (two s, 9H).

Step B. N-Pipecolyl-4-amino-5-benzyloxy-2-oxotetrahydrofuran.

N-(N-tert-Butoxycarbonylpipecolyl)-4-amino-5-benzyloxy-2-oxo-tetrahydrofuran (654 mg) was dissolved in 15 ml of 25% trifluoroacetic acid in dichloromethane and stirred at room temperature. The mixture was concentrated to give a gummy residue. The residue was dissolved in dichloromethane and washed with 10% sodium bicarbonate. The organic layer was dried over anhydrous sodium sulfate, filtered, and concentrated to give 422 mg of the title compound as a beige solid.

1H NMR (500 MHz, $CDCl_3$) 7.38 (m, 5H), 7.15 (d, 1H), 5.55 (d, 1H), 4.95–4.8 (m, 1H), 4.78 (m, 1H), 4.65 (d, 1H), 4.45 (m, 1H), 3.2 (m, 0.5H), 3.05 (m, 0.5H), 2.95 (m, 0.5H), 2.85 (m, 0.5H), 2.65 (m, 1H), 2.55–2.38(m, 1H), 1.95 (m, 1H), 1.8 (m, 1H), 1.6 (m, 2H), 1.38 (m, 2H).

Step C. N-(N-Acetyl-tyrosinyl-valinyl-pipecolyl)-4-amino-5-benzyloxy-2-oxotetrahydrofuran.

N-Acetyl-tyrosinyl-valine (464 mg, 1.44 mmol) and N-Pipecolyl-4-amino-5-benzyloxy-2-oxotetrahydrofuran (412 mg, 1.3 mmol) were dissolved in 5 ml each of dimethylformamide and dichloromethane and cooled to 0° C. To the cooled solution was added 1-hydroxybenzotriazole (HOBT; 210 mg, 1.56 mmol) followed by the addition of 1-(3-dimethylaminopropyl)-3-ethyl carbodiimide hydrochloride (EDC; 326 mg, 1.7 mmol). After stirring for 18 hours, the mixture was diluted with ethyl acetate and washed with water, 10% sodium hydrogen sulfate, 10% sodium bicarbonate, and water. The organic layer was concentrated to give a crude solid that was purified by flash chromatography ($SiO_2$) eluting with 94:6:1 (dichloromethane:isopropanol:pyridine) to give 370 mg of the title compound.

1H NMR (500 MHz, $CD_3OD$ (existing as diastereomers as well as rotomers)) 7.35 (m, 5H), 7.05 (m, 2H), 6.68 (m, 2H), 5.65 & 5.25 (m, 1H), 4.9–3.95 (m, 8H), 3.4–2.6 (m, 4H), 2.5–2.1 (m, 1H), 1.98 (s, 1H), 1.9 (s, 1H), 1.85 (s, 1H), 1.8–1.6 (m, 2H), 1.55–1.3 (m, 4H), 0.95–0.85 (m, 6H).

Step D. N-(N-Acetyl-tyrosinyl-valinyl-pipecolyl)-3-amino-4-oxobutanoic acid.

To a solution of 100 mg of N-(N-Acetyl-tyrosinyl-valinyl-pipecolyl)-4-amino-5-benzyloxy-2-oxotetrahydrofuran in 10 ml of methanol was added 60 mg of $Pd(OH)_2$ on carbon and the mixture placed under an atmosphere of hydrogen via a balloon. The mixture was filtered through Celite and concentrated providing a white solid. This crude solid was dissolved in 2 ml of methanol and triturated with diethyl ether affording 26 mg of the title compound.

1H NMR (500 MHz, CD$_3$OD(existing as diastereomers as well as rotomers)) 7.1 (m, 2H), 6.7 (m, 2H), 5.2 (br. m, 1H), 4.8–3.6 (m, 6H), 3.2–2.5 (m, 4H), 2.5–2.1 (m, 1H), 1.95 (three s, 3H), 1.9–1.3 (m, 6H), 1.1–0.7 (m, 6H).

The following compounds were prepared by a method analogous to that reported for H:

J. N-[N-Acetyl-tyrosinyl-valinyl-(4-hydroxyprolinyl)]-3-amino-4-oxobutanoic acid Substitute N-tert-butoxycarbonyl-4-benzyloxyproline for N-tert-butoxycarbonylpipecolic acid.

L. N-[2-(N-Acetyl-tyrosinyl-valinyl)-(S)-12.3.4-tetrahydroisoquinoline-3-carbonyl]-3-amino-oxobutanoic acid Substitute (S)-N-tert-butoxycarbonyl-1,2,3,4-tetrahydroisoquinoline-3-carboxylic acid for N-tert-butoxycarbonylpipecolic acid.

I. N-(N-Acetyl-tyrosinyl-valinyl-(4-phenoxyprolinyl))-3-amino-4-oxobutanoic acid.

Step A. N-tert-Butoxycarbonyl-4-phenoxyproline methyl ester.

To a cooled solution (0° C.) of N-tert-butoxy-cis-4-hydroxyproline (2–0 g, 8.15 mmol), phenol (0.77 g, 8.15 mmol), and triphenylphosphine (2.14 g, 8.15 mmol) in 20 ml of tetrahydrofuran was added diethyl azodicarboxylate (1.4 ml, 9 mmol) dropwise over 30 minutes. The reaction was stirred at room temperature for 16 hrs. then concentrated to give a viscous residue. The crude residue was purified by flash chromatography (SiO$_2$) eluting with 3:7 (ethyl acetate:hexane) to give 1.89 g of the title compound.

$^1$H NMR (500 MHz, CDCl$_3$) 7.3 (m, 2H), 6.95 (m, 1H), 6.85 (d, 2H), 4.9 (m br., 1H), 4.55–4.15 (m, 2H), 3.88–3.65 (m, 1H), 3.70 (s, 3H), 2.58 (m, 1H), 2.22 (m, 1H), 1.4 (3×s, 9H).

Step B. 4-Phenoxyproline methyl ester hydrochloride.

To a cooled solution (ice bath) of N-tert-Butoxycarbonyl-4-phenoxyproline methyl ester (0.6 g) in 20 ml of ethyl acetate was bubbled anhydrous hydrogen chloride until saturated. The mixture was warmed to room temperature and stirred for 3 hrs. then concentrated to give 480 mg of the title compound.

1H NMR (500 MHz, CDCl$_3$), 7.22 (m, 2H), 6.95 (m 1 H), 6.83 (m, 2H), 5.1 (br., 1H), 4.6 (br. m, 1H), 4.06 (br. m, 1H), 3.75 (s, 3H), 3.55 (br. m, 1H), 2.58 (m, 2H).

Step C. N-Acetyl-tyrosinyl-valinyl-(4-phenoxy)proline methyl ester.

N-Acetyl-tyrosinyl-valine (0.524 g, 1.63 mmol) and 4-phenoxyproline methyl ester (0.381 g, 1.48 mmol) were dissolved in 4 ml each of dimethylformamide and dichloromethane and cooled to 0° C. To the cooled solution was added diisopropylethylamine (258 ul, 1.86 mmol), HOBT (0.24 g, 1.78 mmol), and EDC (0.37 g, 1.92 mmol) and the reaction was stirred for 18 hrs. The mixture was diluted with 400 ml of ethyl acetate and washed with water, 10% sodium hydrogen sulfate, 10% sodium bicarbonate, and water. The organic layer was concentrated to give a residue that was purified by flash chromatography (SiO$_2$) eluting with 94:6:1 (CH2Cl2:i-PrOH:Pyridine) to afford 360 mg of the title compound.

1H NMR (500 MHz, CDCl$_3$ (existing as rotomers)) 7.3 (m, 2H), 7.05 (m, 1H), 6.95 (d, 2H), 6.9–6.2 (4×d, 4H), 5.05 (br. S, 1H), 4.7–3.94 (m,5H), 2.93 (m, 1H), 2.82(m, 1H), 2.65 (m, 1H), 2.2 (m, 1H), 2.05 (m, 1H), 1.95 (s, 3H), 1.86, (m, 1H), 0.98 (d, 3H), 0.88 (d, 3H).

Step D. N-Acetyl-tyrosinyl-valinyl-(4-phenoxy)proline.

Lithium hydroxide (57 mg, 1.37 mmol) was added to a solution of N-Acetyl-tyrosinyl-valinyl-(4-phenoxy)proline methyl ester (360 mg, 0.685 mmol) dissolved in 8 ml of tetrahydrofuran/water (1:1) and stirred at room temperature for 1 hour. The mixture was acidified with 10% hydrochloric acid giving a white precipitate that was collected to give 175 mg of the title compound.

1H NMR (500 MHz, DMSO-d6) 9.2 (br. s, 1H), 8.05–7.95 (m, 2H), 7.3 (m, 1H), 7.0–6.9 (m, 4H), 6.65 (d, 2H), 4.42 (m, 1H), 4.35(m, 1H), 4.05–3.95 (m, 2H), 3.3 (br. s, 2H), 2.75 (m, 1H), 2.55–2.38 (m, 2H), 2.2 (m, 1H), 2.0 (m, 1H), 1.7 (s, 3H), 0.95 (d, 3H), 0.85 (d, 3H).

Step E. N-[N-Acetyl-tyrosinyl-valinyl-(4-phenoxy)prolinyl]-4-amino-5-benzyloxy-2-oxotetrahydrofuran.

The title compound was prepared by the method reported for compound 1, step A, by reaction of N-acetyl-tyrosinyl-valinyl-(4-phenoxy)proline and N-allyloxycarbonyl-4-amino-5-benzyloxytetrahydrofuran.

1H NMR (500 MHz, CDCl$_3$ (existing as a 1:1 diastereomer mixture of the hemiacetal)) 7.8–6.3 (m, 17H), 5.6 (d, 1H), 5.1–4.15 (m, 5H), 4.15–3.75 (m, 2H), 2.95–2.15 (m, 5H), 2.15–1.95 (m, 1H), 1.9–1.85 (2×s, 3H), 1.1–0.75 (m, 6H).

Step F. N-[N-Acetyl-tyrosinyl-valinyl-(4-phenoxy)prolinyl]-3-amino-4-oxobutanoic acid.

The title compound was prepared by the hydrogenolysis procedure reported for compound 1, step D.

1H NMR (500 MHz, CD$_3$OD (existing as a 1:1 diastereomer mixture of the hemiacetal)) 7.25 (m, 2H), 7.10–6.85 (m, 5H), 6.65 (d, 2H), 5.1 (br. m, 1H), 4.65–4.05 (m, 5H), 4.0–3.40 (m, 2H), 2.95–2.35 (m, 5H), 2.25 (m, 1H), 2.05 (m, 1H), 1.85 (s, 3H), 1.0 (d, 3H), 0.95 (d, 3H).

K. N-[N-Acetyl-tyrosinyl-valinyl-(4-benzyloxy)prolinyl]-3-amino-4-oxobutanoic acid.

Step A. N-(N-Allyloxycarbonyl-4-benzyloxyprolinyl)-3-amino-4-oxobutanoic acid tert-butyl ester semicarbazone.

The title compound was prepared by the reaction of N-allyloxycarbonyl-4-benzyloxyproline and 3-amino-4-oxobutanoic acid tert-butyl ester semicarbazone (T. L. Graybill et. al., Abstracts of papers, 206th National Meeting of the American Chemical Society, Abstract MEDI-235. Chicago, Ill.(1993)) under similar peptide coupling conditions as reported above.

1H NMR (500 MHz, CDCl$_3$) 9.05 (br. s, 1H), 7.85 (br. m, 1H), 7.4–7.2 (m, 5H), 7.15 (br. s, 1H), 6.55 (br. s, 1H), 5.9 (m, 1H), 5.1–4.9 (br. m, 2H), 4.65–4.4 (m, 4H), 4.2 (br. m, 1H), 3.75–3.5 (m, 2H), 2.75–2.55 (m, 2H), 2.5 (br. m, 1H), 2.25 (br. m, 1H) 1.4 (s, 9H).

Step B. N-(N-Acetyl-tyrosinyl-valinyl-(4-benzyloxyprolinyl))-3-amino-4-oxobutanoic acid tert-butyl ester semicarbazone.

The title compound was prepared by reaction of N-acetyl-tyrosinyl-valine and N-(N-allyloxycarbonyl-4-benzyloxyprolinyl)-3-amino-4-oxobutanoic acid tert-butyl ester semicarbazone by reaction conditions reported for compound 1, step A.

1H NMR (500MHz, CD$_3$OD) 7.35–7.2 (m, 6H), 7.0 (d, 2H), 6.65(d, 2H), 4.85 (m, 1H), 4.6–4.45 (m, 4H), 4.3 (br. m, 1H), 4.15 (m, 1H), 3.7 (m, 1H), 2.95 (m, 1H), 2.75–2.6 (m, 3H), 2.35 (m, 1H), 2.1 (m, 1H), 1.9 (s, 3H), 1.4 (s, 9H), 0.95 (d, 3H), 0.90 (s, 3H).

Step C. N-(N-Acetyl-tyrosinyl-valinyl-(4-benzyloxyprolinyl))-3-amino-4-oxobutanoic acid.

N-(N-Acetyl-tyrosinyl-valinyl-(4-benzyloxyprolinyl))-3-amino-4-oxobutanoic acid tert-butyl ester semicarbazone (270 mg) was dissolved into 10 ml of 25% trifluoroacetic acid in dichloromethane and stirred at room temperature for 3 hours. The mixture was concentrated to give a solid residue. The residue was dissolved into a 10 ml mixture of methanol:acetic acid:37% formaldehyde (3:1:1) and stirred at room temperature for 1 hour. The mixture was concentrated and the resulting residue purified by flash chromatography (SiO$_2$) eluting with dichloromethane/methanol/formic acid (100:5:0.5) to give 37 mg of the title compound.

1H NMR (500 MHz, CD$_3$OD (existing as a 1:1 mixture of diastereomers of the hemiacetal)) 7.4–7.25 (m, 5H), 7.0 (d, 2H), 6.65 (d, 2H), 4.65–4.05 (m, 7H), 3.75–3.4 (m, 2H), 3.05–2.3 (m, 5H), 2.2–1.95 (m, 2H), 1.90 (s, 3H), 1.0 (d, 3H), 0.95 (d, 3H).

The data of the examples above demonstrate that compounds according to this invention display inhibitory activity towards IL-1β.

Insofar as the compounds of this invention are able to inhibit ICE in vitro and furthermore, may be delivered orally to mammals, they are of evident clinical utility for the treatment of IL-1 mediated diseases. These tests are predictive of the compounds ability to inhibit ICE in vivo.

While we have described a number of embodiments of this invention, it is apparent that our basic constructions may be altered to provide other embodiments which utilize the products and processes of this invention. Therefore, it will be appreciated that the scope of this invention is to be defined by the appended claims, rather than by the specific embodiments which have been presented by way of example.

We claim:

1. A method for selecting an ICE inhibitor comprising the steps of:

a) selecting a candidate compound of defined chemical structure comprising at least two hydrogen bonding moieties, at least two hydrophobic moieties, and one electronegative moiety comprising one or more electronegative atoms attached either to the same atom or to adjacent atoms in the electronegative moiety, wherein the chemical structure comprising at least two hydrogen bonding moieties is selected from the group consisting of:

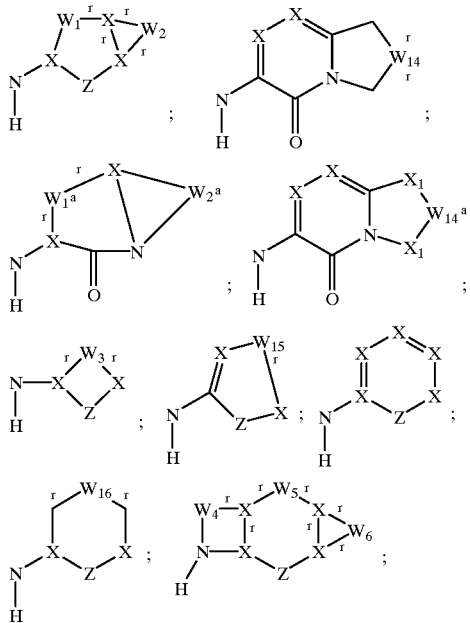

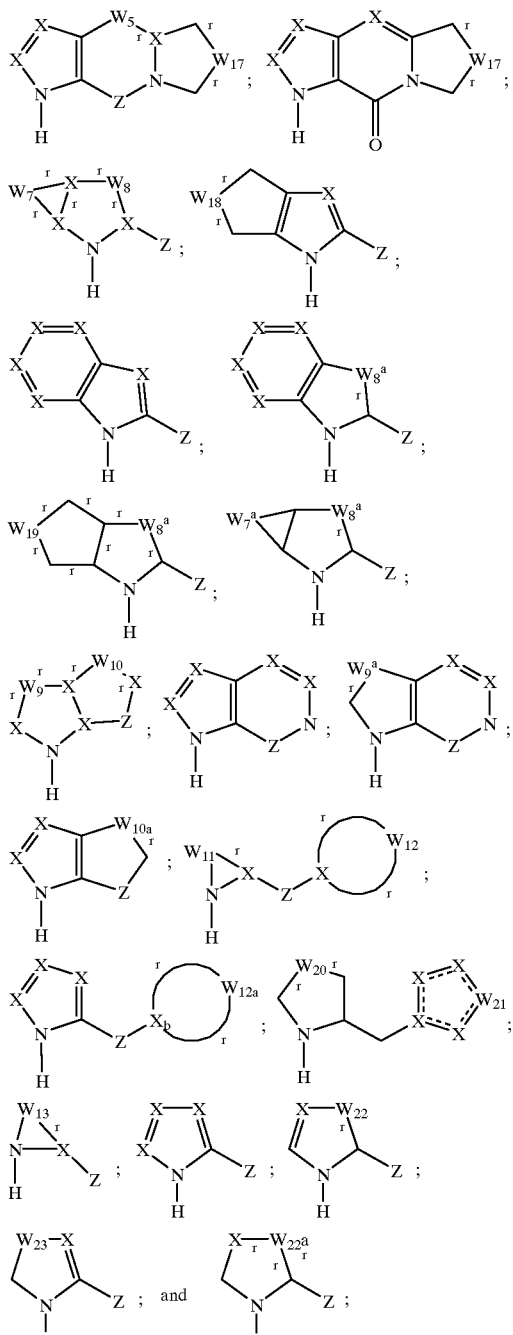

wherein.

each X is independently C or N;

each Z is CO or SO$_2$;

W$_1$ is a straight chain comprising 1–3 covalently bound members independently selected from the group consisting of C, N, S and O, said covalent bonds between said members being independently saturated or unsaturated and said chain comprising two ends which are covalently bound to two different X atoms through bonds r;

W$_2$ is a straight chain comprising 3–5 covalently bound members independently selected from the group consisting of C, N, S and O, said covalent bonds between said members being independently saturated or unsaturated and said chain comprising two ends which are covalently bound to two different X atoms through bonds r;

each bond labeled r is independently a single or a double bond, $W_{14}$ is a straight chain comprising 1–3 covalently bound members independently selected from the group consisting of C, N, S and O, said covalent bonds between said members being independently saturated or unsaturated and said chain comprising two ends which are covalently bound to two different C atoms through bonds r;

$W_{1a}$ is a straight chain comprising 1–3 covalently bound members independently selected from the group consisting of C, N, S and O, said covalent bonds between said members being independently saturated or unsaturated and said chain comprising two ends which are covalently bound to two different X atoms through bonds r;

$W_{2a}$ is a straight chain comprising 3–4 covalently bound members independently selected from the group consisting of C, N, S and O, said chain comprising two ends which are covalently bound to two different atoms to form an aryl or heteroaromatic ring therewith;

each $X_1$ is independently C, N, or O;

$W_{14a}$ is a straight chain comprising 1–3 covalently bound members independently selected from the group consisting of C, N, S and O, said covalent bonds between said members being saturated or unsaturated and said chain comprising two ends which are covalently bound to two different $X_1$ atoms to form a non-aromatic ring therewith;

$W_3$ is a straight chain comprising 24 covalently bound members independently selected from the group consisting of C, N, S and O, said covalent bonds between said members being independently saturated or unsaturated and said chain comprising two ends which are covalently bound to two different X atoms through bonds r;

$W_{15}$ is a straight chain comprising 1–2 covalently bound members independently selected from the group consisting of C, N, S and O, said covalent bonds between said members being independently saturated or unsaturated and said chain comprising two ends which are covalently bound to two different X atoms;

$W_{16}$ is a straight chain comprising 1–2 covalently bound members independently selected from the group consisting of C, N, S and O, said covalent bonds between said members being independently saturated or unsaturated and said chain comprising two ends which are covalently bound to two different C atoms through bonds r;

$W_4$ is a straight chain comprising 2–4 covalently bound members independently selected from the group consisting of C, N, S and O, said covalent bonds between said members being independently saturated or unsaturated and said chain comprising two ends which are covalently bound to two different atoms, each $W_5$ is a direct bond or a straight chain comprising 1–2 covalently bound members independently selected from the group consisting of C, N, S and O, said covalent bonds between said members being independently saturated or unsaturated and said chain comprising two ends which are covalently bound to two different atoms through bonds r, $W_6$ is a straight chain comprising 3–5 covalently bound members independently selected from the group consisting of C, N, S and O, said covalent bonds between said members being independently saturated or unsaturated and said chain comprising two ends which are covalently bound to two different X atoms through bonds r;

each $W_{17}$ is a straight chain comprising 1–3 covalently bound members independently selected from the group consisting of C, N, S and O, said covalent bonds between said members being independently saturated or unsaturated and said chain comprising two ends which are covalently bound to two different C atoms through bonds r;

$W_7$ is a straight chain comprising 3–5 covalently bound members independently selected from the group consisting of C, N, S and O, said covalent bonds between said members being independently saturated or unsaturated and said chain comprising two ends which are covalently bound to two different X atoms through bonds r;

$W_8$ is a straight chain comprising 1–3 covalently bound members independently selected from the group consisting of C, N, S and O, said covalent bonds between said members being independently saturated or unsaturated, and said chain comprising two ends which are covalently bound to two different X atoms through bonds r;

$W_{18}$ is a straight chain comprising 1–3 covalently bound members independently selected from the group consisting of C, N, S and O, said covalent bonds between said members being independently saturated or unsaturated and said chain comprising two ends which are covalently bound to two different C atoms through bonds r;

each $W_{8a}$ is a straight chain comprising 1–3 covalently bound members independently selected from the group consisting of C, N, S and O, said covalent bonds between said members being independently saturated or unsaturated and said chain comprising two ends which are covalently bound to two different C atoms, $W_{19}$ is a straight chain comprising 1–3 covalently bound members independently selected from the group consisting of C, N, S and O, said covalent bonds between said members being independently saturated or unsaturated and said chain comprising two ends which are covalently bound to two different C atoms through bonds r;

$W_{7a}$ is a straight chain comprising 3 covalently bound members independently selected from the group consisting of C, N, S and O, said chain comprising two ends which are covalently bound to two different C atoms to form an aryl ring therewith;

$W_9$ is a straight chain comprising 1–3 covalently bound members independently selected from the group consisting of C, N, S and O, said covalent bonds between said members being independently saturated or unsaturated and said chain comprising two ends which are covalently bound to two different X atoms through bonds r;

$W_{10}$ is a straight chain comprising 1–3 covalently bound members independently selected from the group consisting of C, N, S and O, said covalent bonds between said members being independently saturated or unsaturated and said chain comprising two ends which are covalently bound to two different X atoms through bonds r;

$W_{9a}$ is a straight chain comprising 1–3 covalently bound members independently selected from the group consisting of C, N, S and O, said covalent bonds between said members being independently saturated or unsaturated and said chain comprising two ends which are covalently bound to two different C atoms;

$W_{10a}$ is a straight chain comprising 1–3 covalently bound members independently selected from the group consisting of C, N, S and O, said covalent bonds between said members being independently saturated or unsaturated and said chain comprising two ends which are covalently bound to two different X atoms; and $W_{11}$ is a straight chain comprising 3–5 covalently bound members independently selected from the group consisting of C, N, S and O, said covalent bonds between said members being independently saturated or unsaturated and said chain comprising two ends which are covalently bound to two different atoms to form a ring which may optionally be benzofused or pyridinofused;

$W_{12}$ is a straight chain comprising 4–6 covalently bound members independently selected from the group consisting of C, N, S and O, said covalent bonds between said members being independently saturated or unsaturated and said chain comprising two ends which are covalently bound to the indicated X atom through bonds r;

each $X_b$ is independently C or N;

$W_{12a}$ is a straight chain comprising 4–6 covalently bound members independently selected from the group consisting of C, N, S and O, said covalent bonds between said members being independently saturated or unsaturated and said chain comprising two ends which are covalently bound to the indicated $X_b$ atom through bonds r; and $W_{20}$ is a straight chain comprising 1–3 covalently bound members independently selected from the group consisting of C, N, S and O, said covalent bonds between said members being independently saturated or unsaturated and said chain comprising two ends which are covalently bound to two different C atoms through bonds r;

$W_{21}$ is a straight chain comprising 1–2 covalently bound members independently selected from the group consisting of C, N, S and O, said chain comprising two ends which are covalently bound to two different C atoms to form an aryl ring therewith;

$W_{13}$ is a straight chain comprising 3–5 covalently bound members independently selected from the group consisting of C, N, S and O, said covalent bonds between said members being independently saturated or unsaturated and said chain comprising two ends which are covalently bound to two different atoms, $W_{22}$ is a straight chain comprising 1–3 covalently bound members independently selected from the group consisting of C, N, S and O, said covalent bonds between said members being independently saturated or unsaturated and said chain comprising two ends which are covalently bound to two different atoms;

$W_{23}$ is a straight chain comprising 1–3 covalently bound members independently selected from the group consisting of C, N, S and O, said covalent bonds between said members being independently saturated or unsaturated and said chain comprising two ends which are covalently bound to two different atoms; and $W_{22a}$ is a straight chain comprising 1–3 covalently bound members independently selected from the group consisting of C, N, S and O, said covalent bonds between said members being independently saturated or unsaturated and said chain comprising two ends which are covalently bound to two different atoms through bonds r;

b) determining a low-energy conformation for binding of said compound to the active site of ICE, c) evaluating the capability of said compound in said conformation to form at least two hydrogen bonds with the amide —NH— groups or the carbonyl-C(=O)- groups of Arg-341 and Ser-339 of ICE, d) evaluating the capability of said compound in said conformation to associate with at least two of the binding pockets of ICE selected from the group consisting of the P2 binding pocket, the P3 binding pocket, the P4 binding pocket and the P' binding pocket;

e) evaluating the capability of said compound in said conformation to interact with the P1 binding pocket of ICE; and f) accepting or rejecting said candidate compound as an ICE inhibitor based on the determinations and evaluations carried out in steps a) through e);

wherein:

1) one of said hydrophobic moieties associates with the P2 binding pocket of ICE, in such a way that:
   i) the distance from the center of mass of the hydrophobic moiety in the P2 binding pocket to the carbonyl oxygen of Arg-341 of ICE is between about 7.1 Å and about 12.5 Å;
   ii) the distance from the center of mass of the hydrophobic moiety in the P2 binding pocket to the amide nitrogen of Arg-341 of ICE is between about 6.0 Å and about 12 Å; and
   iii) the distance from the center of mass of the hydrophobic moiety in the P2 binding pocket to the carbonyl oxygen of Ser-339 of ICE is between about 3.7 Å and about 9.5 Å;

2) one of said hydrophobic moieties associates with the P3 binding pocket of ICE in such a way that:
   i) the distance from the center of mass of the hydrophobic moiety in the P3 binding pocket to the carbonyl oxygen of Arg-341 of ICE is between about 3.9 Å and about 9.5 Å;
   ii) the distance from the center of mass of the hydrophobic moiety in the P3 binding pocket to the amide nitrogen of Arg-341 of ICE is between about 4 Å and about 13 Å; and
   iii) the distance from the center of mass of the hydrophobic moiety in the P3 binding pocket to the carbonyl oxygen of Ser-339 of ICE is between about 7.0 Å and about 13 Å;

3) one of said hydrophobic moieties associates with the P4 binding pocket of ICE in such a way that:
   i) the distance from the center of mass of the hydrophobic moiety in the P4 binding pocket to the carbonyl oxygen of Arg-341 of ICE is between about 4.5 Å and about 7.5 Å;
   ii) the distance from the center of mass of the hydrophobic moiety in the P4 binding pocket to the amide nitrogen of Arg-341 of ICE is between about 5.5 Å and about 8.5 Å; and
   iii) the distance from the center of mass of the hydrophobic moiety in the P4 binding pocket to the carbonyl oxygen of Ser-339 of ICE is between about 8 Å and about 11 Å; and 4) one of said hydrophobic moieties associates with the P' binding pocket of ICE in such a way that:
   i) the distance from the center of mass of the hydrophobic moiety in the P' binding pocket to the carbonyl oxygen of Arg-341 of ICE is between about 11 Å and about 16 Å;
   ii) the distance from the center of mass of the hydrophobic moiety in the P' binding pocket to the amide nitrogen of Arg-341 of ICE is between about 10 Å and about 15 Å; and
   iii) the distance from the center of mass of the hydrophobic moiety in the P' binding pocket to the carbonyl oxygen of Ser-339 of ICE is between about 8 Å and about 12 Å.

2. The method of claim 1, additionally comprising the following steps which follow step e) and preceed step f):
   g) evaluating the deformation energy of binding of said compound to ICE; and
   h) evaluating the contribution of the sum of all electrostatic interactions between said compound and ICE when said compound is bound thereto in said conformation.

* * * * *